US008346343B2

(12) United States Patent
Kimura et al.

(10) Patent No.: US 8,346,343 B2
(45) Date of Patent: Jan. 1, 2013

(54) MEDICAL DEVICE MAGNETIC GUIDANCE/POSITION DETECTION SYSTEM

(75) Inventors: Atsushi Kimura, Tokyo (JP); Akio Uchiyama, Kanagawa (JP); Ryoji Sato, Tokyo (JP)

(73) Assignees: Olympus Corporation, Tokyo (JP); Olympus Medical Systems Corp., Tokyo (JP)

( * ) Notice: Subject to any disclaimer, the term of this patent is extended or adjusted under 35 U.S.C. 154(b) by 1033 days.

(21) Appl. No.: 11/633,282

(22) Filed: Dec. 4, 2006

(65) Prior Publication Data

US 2007/0185398 A1 Aug. 9, 2007

Related U.S. Application Data

(63) Continuation of application No. PCT/JP2005/023550, filed on Dec. 16, 2005.

(30) Foreign Application Priority Data

Aug. 8, 2005 (JP) ................................. 2005-229474
Dec. 2, 2005 (JP) ................................. 2005-349179

(51) Int. Cl.
*A61B 5/05* (2006.01)
(52) U.S. Cl. ........................................ 600/424; 128/899
(58) Field of Classification Search .................. 600/424, 600/109, 114, 118, 160; 128/899; 604/890.1; 348/76, 77
See application file for complete search history.

(56) References Cited

U.S. PATENT DOCUMENTS

| 5,592,939 | A | 1/1997 | Martinelli |
| 6,847,837 | B1 | 1/2005 | Meizer et al. |
| 6,930,481 | B2 * | 8/2005 | Okamoto et al. ............. 324/318 |
| 2003/0114742 | A1 * | 6/2003 | Lewkowicz et al. .......... 600/407 |
| 2003/0229268 | A1 | 12/2003 | Uchiyama et al. |
| 2007/0004994 | A1 * | 1/2007 | Sherman ........................ 602/26 |

FOREIGN PATENT DOCUMENTS

| JP | 6-285044 | 10/1994 |
| JP | 09-028662 | 2/1997 |

(Continued)

OTHER PUBLICATIONS

Tokunaga, Y., et al., "Precision Position-Detecting System Using an LC Resonant Magnetic Marker", Journal of the Magnetics of Society of Japan, 29, pp. 153-156 (2005) with English Translation of Japanese Publication.
Chinese Office Action dated Mar. 24, 2011, together with English Translation.
United States Office Action dated Dec. 23, 2009 issued in related U.S. Appl. No. 11/633,282.

(Continued)

*Primary Examiner* — Brian Casler
*Assistant Examiner* — Daniel Huntley
(74) *Attorney, Agent, or Firm* — Scully Scott Murphy & Presser, PC

(57) ABSTRACT

A medical-device magnetic guiding position detecting system that can prevent a decrease in the strength of a position detecting magnetic field in an operating area of a medical device is provided. The medical-device magnetic guiding position detecting system includes a medical device that is disposed in the body of a subject and that includes at least one magnet and a circuit including an internal coil, a first magnetic field generating unit for generating a first magnetic field in the operating area of the medical device, position detecting means for detecting an induction magnetic field induced in the internal coil due to the first magnetic field, and at least one pair of opposing coils for generating a second magnetic field that acts on the at least one magnet. The opposing coils forming each of the at least one pair are independently driven.

6 Claims, 18 Drawing Sheets

FOREIGN PATENT DOCUMENTS

| | | |
|---|---|---|
| JP | 2001-179700 | 7/2001 |
| JP | 3321235 | 6/2002 |
| JP | 2002-187100 | 7/2002 |
| JP | 2003-197436 A | 7/2003 |
| JP | 2004-229922 | 8/2004 |
| WO | WO 2004/014225 | 2/2004 |

OTHER PUBLICATIONS

International Search Report PCT/JP2005/023550 dated Apr. 28, 2006.

English language abstract only of JP 06-285044 A published Oct. 11, 1994.

* cited by examiner

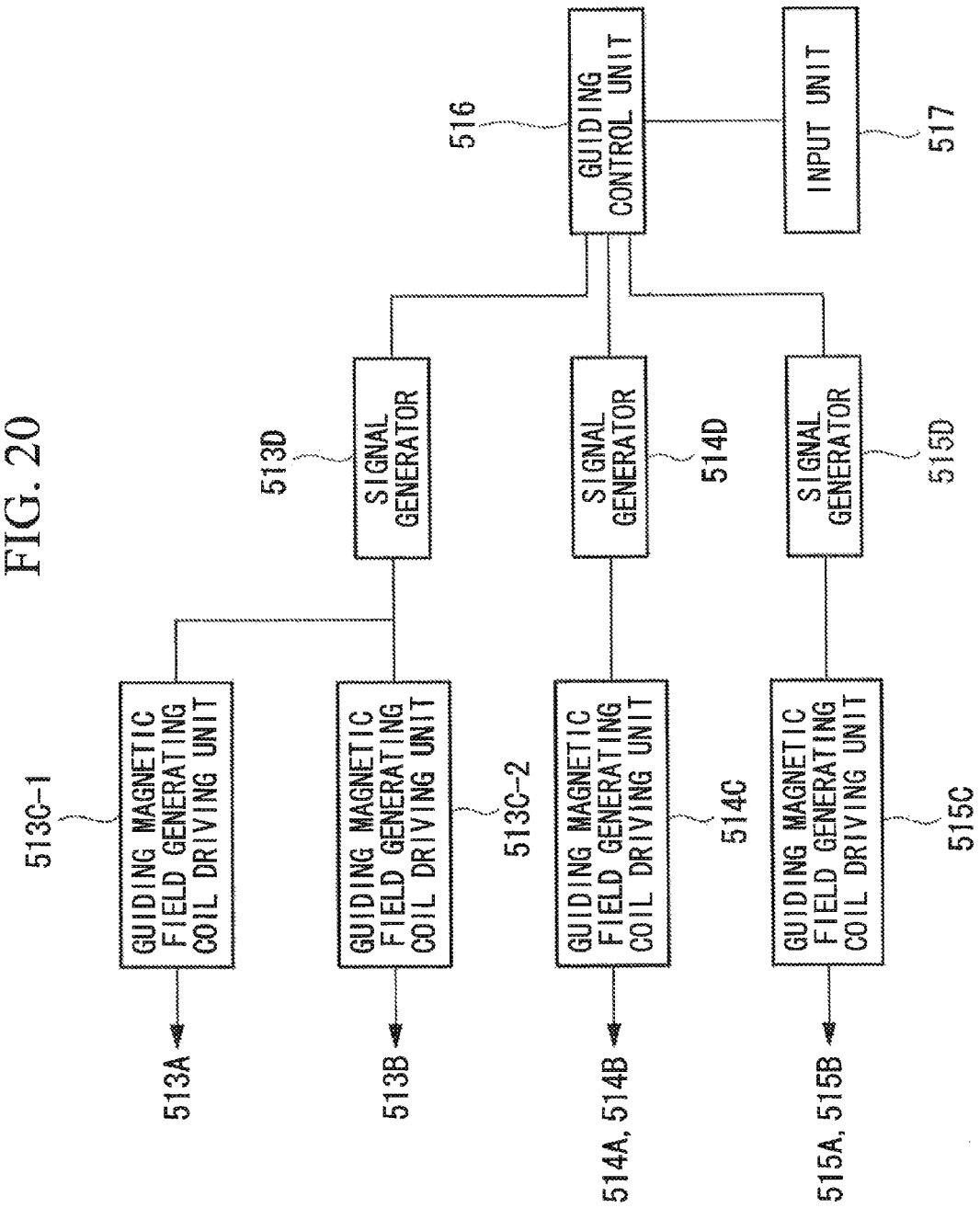

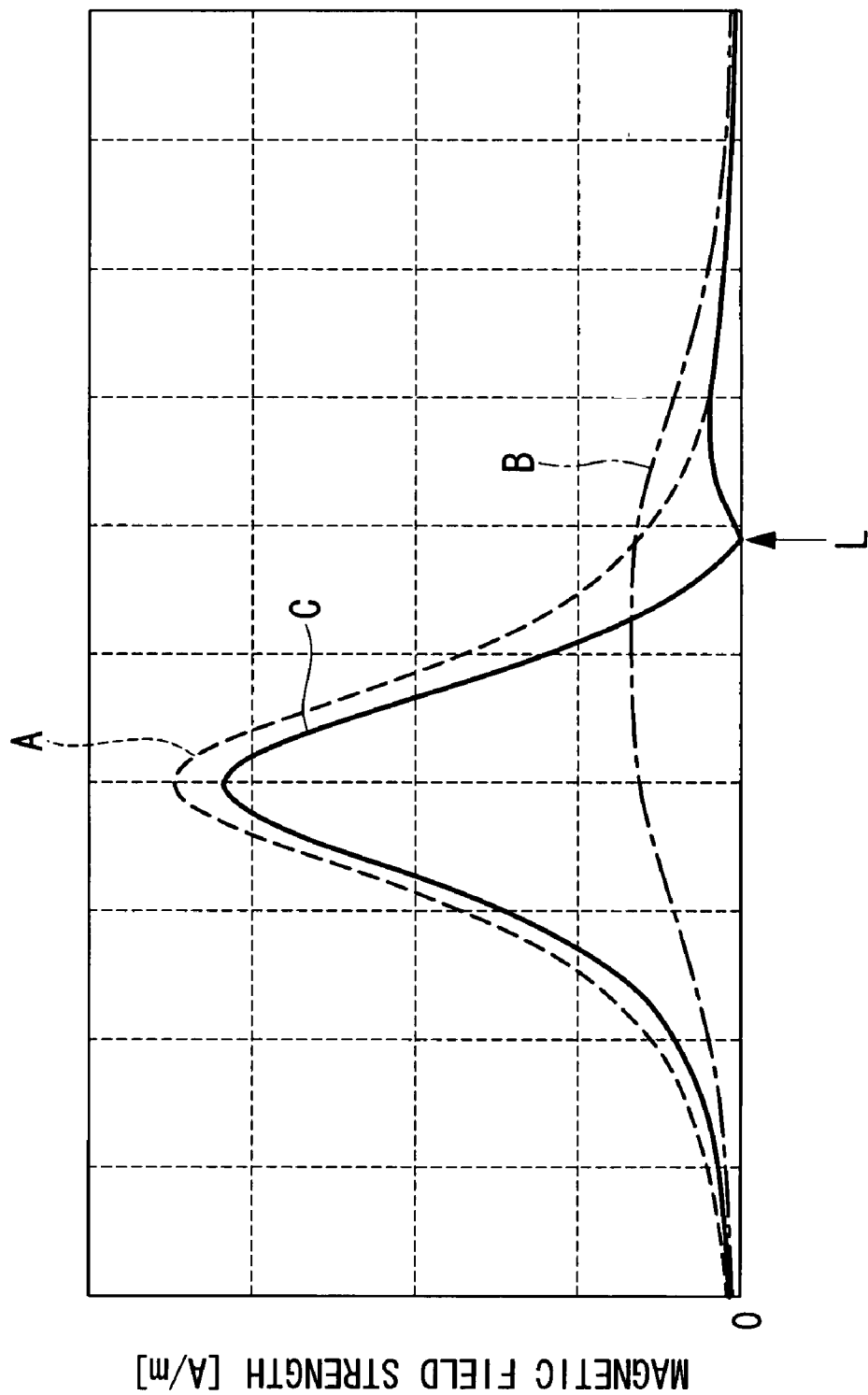

MEDICAL DEVICE MAGNETIC GUIDANCE/POSITION DETECTION SYSTEM

This application is a continuation application of PCT/JP2005/023550 filed on Dec. 16, 2005, which is based on Japanese Patent Applications Nos. 2005-349179 and 2005-229474, the contents of each of which are incorporated herein by reference.

BACKGROUND OF THE INVENTION

1. Field of the Invention

The present invention relates to a medical-device magnetic guiding position detecting system.

2. Description of Related Art

In recent years, a medical device that is swallowable by a subject, such as an examinee, has been researched and developed for practical use. The medical device is capable of passing through a body lumen of the subject so as to capture an image of a target location in the body lumen. An example of the medical device is a swallowable endoscopic capsule.

In order to guide such a medical device to the target location in the body lumen, means for detecting the current position of the medical device in the body lumen and guiding the medical device to the target location is required.

As the means for guiding the medical device to the target location, means is known in which a magnet is mounted in an endoscope and the position of the endoscope is controlled by externally applying a magnetic field to the magnet.

To detect the position of the medical device, a method for magnetically detecting the position is known. A magnetic position detecting method is known in which a magnetic field is externally applied to a subject having a coil therein and a magnetic field generated by an electromotive force induced by the applied magnetic field is detected using an external magnetic sensor. Refer to, for example, the following Document 1 and Document 2:

Document 1: Japanese Unexamined Patent Application, Publication No. Hei 6-285044

Document 2: "Precision Position-Detecting System Using Wireless LC Resonant Magnetic Marker", TOKUNAGA, HASHI, YABUKAMI, KONO, TOYODA, OZAWA, OKAZAKI, and ARAI, Journal of the Magnetic Society of Japan, vol. 29, p 153-156, 2005.

Document 1 describes a technology in which a substantially rectangular parallelepiped magnetic field source (a magnetic field generating coil for detecting a position) including three magnetic field generating coils whose axes are perpendicular to each other is disposed outside a body and, a magnetic field detecting coil including three magnetic field reception coils whose axes are perpendicular to each other is disposed in a medical capsule. According to this technology, the magnetic field source generates an alternating magnetic field, which induces an electrical current in the magnetic field detection coil. The position of the magnetic field detecting coil, i.e., the position of the medical capsule can be detected on the basis of the induced electrical current.

In contrast, Document 2 describes a position detecting system including an exciting coil (a position detecting magnetic field generating coil) that generates an alternating magnetic field, an LC resonant magnetic marker that generates an induced magnetic field in response to the reception of the alternating magnetic field, and a detection coil that detects the induced magnetic field. In this position detecting system, the LC resonant magnetic marker resonates at a predetermined frequency in accordance with an additional capacitance and a parasitic capacitance. Accordingly, if the frequency of the alternating magnetic field is set so as to be equal to the predetermined frequency, the strength of the induced magnetic field can be significantly increased compared with another frequency, and therefore, the detection efficiency can be increased.

However, in the case where the technologies described in Documents 1 and 2 are combined with an technology in which a magnetic field is used for guiding the medical capsule, if the center axis line of a guiding magnetic field generating coil for generating a guiding magnetic field is substantially coincident with that of the position detecting magnetic field generating coil, mutual induction may occur between the position detecting magnetic field generating coil and the guiding magnetic field generating coil in accordance with a time-varying change in the alternating magnetic field generated by the position detecting magnetic field generating coil.

That is, an electromotive force generated in the guiding magnetic field generating coil by the mutual induction causes an electrical current to flow in a closed circuit formed by the guiding magnetic field generating coil and a driving unit for driving the guiding coil. This electrical current disadvantageously generates a magnetic field that cancels out the above-described alternating magnetic field.

In addition, in order to make the distribution of a magnetic field in a guiding space uniform, the structure of the guiding magnetic field generating coil, in general, is of the Helmholtz type or a type similar to the Helmholtz type. In general, two guiding magnetic field generating coils are connected to the driving unit of a guiding coil in series. In such a case, even when an electromotive force due to the mutual induction is generated in only one of the two guiding magnetic field generating coils, a closed circuit is formed by the driving unit of a guiding coil. Accordingly, an electrical current flows in the other guiding magnetic field generating coil. For this reason, a magnetic field having a phase substantially opposite to that of the position detecting magnetic field is widely distributed in the guiding space.

At that time, as shown in FIG. 21, a combined magnetic field (shown by a solid line C) composed of the position detecting magnetic field (shown by a dotted line A) emanating from the position detecting magnetic field generating coil and the guiding magnetic field (shown by a dotted line B) emanating from the guiding magnetic field generating coil passes through the coil incorporated in the capsule. In particular, depending on a relationship between the positions of the position detecting magnetic field generating coil and the guiding magnetic field generating coil, the position detecting magnetic field (shown by the dotted line A) could be substantially completely canceled out by the guiding magnetic field (shown by the dotted line B) in an area (L) even within the operational area of the medical device. Since no magnetic fields pass through the coil incorporated in the capsule, no induced electrical currents flow in the coil. Therefore, no induced magnetic fields occur in the coil. As a result, the position of the medical capsule cannot be detected in that area.

BRIEF SUMMARY OF THE INVENTION

Accordingly, it is an object of the present invention to provide a medical-device magnetic guiding and position detecting system that can prevent a decrease in the strength of the position detecting magnetic field within the operational range of the medical device.

To achieve this object, the present invention provides the following means.

According to a first aspect of the present invention, a medical-device magnetic guiding and position detecting system includes a medical device disposed in the body of a subject, where the medical device includes at least one magnet and a circuit including an internal coil, a first magnetic field generating unit for generating a first magnetic field, position detecting means for detecting an induction magnetic field induced in the internal coil due to the first magnetic field, and at least one pair of opposing coils for generating a second magnetic field that acts on the at least one magnet. The opposing coils forming each of the at least one pair are independently driven.

According to the first aspect of the present invention, the opposing coils forming each of the at least one pair are independently driven. Therefore, even when the condition under which mutual induction due to the first magnetic field is induced in one of the opposing coils occurs, an electrical current generated by the electromotive force due to the mutual induction does not flow from the one of the opposing coils to the other. As a result, the other coil does not produce a magnetic field having a phase that is the same as that of the mutual induction magnetic field having a reversed phase to that of the first magnetic field. In this way, only the second magnetic field is produced.

Since the other coil does not produce a magnetic field that cancels out the first magnetic field, formation of an area where the first magnetic field is substantially zero can be prevented. As a result, formation of an area where an induction magnetic field in the internal coil does not occur can be prevented.

According to a second aspect of the present invention, a medical-device magnetic guiding and position detecting system includes a medical device disposed in the body of a subject, where the medical device includes at least one magnet and a circuit including an internal coil, a first magnetic field generating unit for generating a first magnetic field, position detecting means for detecting an induction magnetic field induced in the internal coil due to the first magnetic field, at least one pair of opposing coils for generating a second magnetic field that acts on the at least one magnet, and a switching unit electrically connected to the at least one pair of opposing coils. The switching unit is in a disconnecting mode only when the position detecting means detects the position of the internal coil.

According to the second aspect of the present invention, the switching unit is in a disconnecting mode only when the position detecting means detects the position of the internal coil. Therefore, even when the condition under which mutual induction due to the first magnetic field is induced in each of the at least one pair of opposing coils occurs, the occurrence of a mutual induction magnetic field can be prevented. In contrast, when the position detecting means does not detect the position of the internal coil, the switching unit is in a connecting mode. Accordingly, the at least one pair of opposing coils can generate the second magnetic field.

According to a third aspect of the present invention, a medical-device magnetic guiding and position detecting system includes a medical device disposed in the body of a subject, where the medical device includes at least one magnet and a circuit including an internal coil, a first magnetic field generating unit for generating a first magnetic field, position detecting means for detecting an induction magnetic field induced in the internal coil due to the first magnetic field, and at least one pair of opposing coils for generating a second magnetic field that acts on the at least one magnet. The opposing coils forming each of the at least one pair are driven in parallel.

According to the third aspect of the present invention, the opposing coils forming each of the at least one pair are driven in parallel. Therefore, even when the condition under which mutual induction due to the first magnetic field is induced in one of the opposing coils occurs, an electrical current generated by the electromotive force due to the mutual induction does not flow from the one of the opposing coils to the other. As a result, the other coil does not produce a magnetic field having a phase that is the same as that of the mutual induction magnetic field having a reversed phase to that of the first magnetic field. In this way, only the second magnetic field is produced.

Since the other coil does not produce a magnetic field that cancels out the first magnetic field, formation of an area where the first magnetic field is substantially zero can be prevented. As a result, formation of an area where an induction magnetic field in the internal coil does not occur can be prevented.

According to a fourth aspect of the present invention, a medical-device magnetic guiding and position detecting system includes a medical device disposed in the body of a subject, where the medical device includes at least one magnet and a circuit including an internal coil, a first magnetic field generating unit for generating a first magnetic field, position detecting means for detecting an induction magnetic field induced in the internal coil due to the first magnetic field, at least one pair of opposing coils for generating a second magnetic field that acts on the at least one magnet, and an element having an impedance lower than an impedance of one of the two opposing coils forming each of the at least one pair at least at a frequency of the first magnetic field. In addition, the element has an impedance higher than an impedance of the other opposing coil at least at a frequency of the second magnetic field. The opposing coils forming each of the at least one pair form a series-connected circuit. One terminal of the element is connected to a point between the opposing coils of each of the at least one pair, and the other terminal of the element is connected to ground.

According to the fourth aspect of the present invention, one terminal of the element is connected to a point between the opposing coils of each of the at least one pair, and the other terminal of the element is connected to ground. Therefore, even when the condition under which mutual induction due to the first magnetic field is induced in one of the opposing coils occurs, an electrical current generated by the electromotive force due to the mutual induction does not flow from the one of the opposing coils to the other.

Since the element has an impedance lower than an impedance of one of the two opposing coils forming each of the at least one pair at least at a frequency of the first magnetic field, an electrical current generated by the electromotive force due to the mutual induction does not flow from the one of the opposing coils to the other, but flows into the element. That is, since a closed circuit is formed by the one of the opposing coils and the element, the electrical current generated by the electromotive force due to the mutual induction does not flow from the one of the opposing coils to the other.

As a result, the other coil does not produce a magnetic field having a phase that is the same as that of the mutual induction magnetic field having a reversed phase to that of the first magnetic field. In this way, only the second magnetic field is produced.

Consequently, since the other coil does not produce a magnetic field that cancels out the first magnetic field, formation of an area where the first magnetic field is substantially zero can be prevented. As a result, formation of an area where an induction magnetic field in the internal coil does not occur can be prevented.

In addition, since the element has an impedance higher than an impedance of the other opposing coil at least at a frequency of the second magnetic field, an electrical current for generating the second magnetic field flows in the at least one of the pair of opposing coils. Thus, this electrical current does not flow in the element. Consequently, each of the at least one pair of opposing coils can generate the second magnetic field.

According to the fourth aspect of the present invention, it is desirable that the frequency of the first magnetic field is higher than that of the second magnetic field and the impedance of the element decreases as the frequency increases.

In such a configuration, the impedance of the element is lower than that of one of the opposing coils at least at a frequency of the first magnetic field. Therefore, even when the condition under which mutual induction due to the first magnetic field is induced in one of the opposing coils occurs, an electrical current generated by the electromotive force due to the mutual induction does not flow from the one of the opposing coils to the other.

That is, since a closed circuit is formed by the one of the opposing coils and the element at the frequency of the first magnetic field, the electrical current due to the mutual induction does not flow from the one of the opposing coils to the other.

In contrast, the impedance of the element is higher than that of one of the opposing coils at least at a frequency of the second magnetic field. Therefore, an electrical current for generating the second magnetic field flows in the opposing coils. Thus, this electrical current does not flow in the element. Consequently, each of the at least one pair of opposing coils can generate the second magnetic field.

According to the fourth aspect of the present invention, it is desirable that the element is a series resonance circuit that produces resonance at a resonance frequency and the resonance frequency of the series resonance circuit is substantially the same as the frequency of the first magnetic field.

In such a configuration, the element is a series resonance circuit having a resonance frequency that is substantially the same as the frequency of the first magnetic field. Therefore, even when the condition under which mutual induction due to the first magnetic field is induced in one of the opposing coils occurs, an electrical current generated by the electromotive force due to the mutual induction does not flow from the one of the opposing coils to the other.

That is, since a closed circuit is formed by the one of the opposing coils and the element, which is a series resonance circuit, at the frequency of the first magnetic field, the electrical current due to the mutual induction does not flow from the one of the opposing coils to the other.

In contrast, at a frequency other than the frequency of the first magnetic field, for example, at the frequency of the second magnetic field, the impedance of the element, which is a series resonance circuit, is higher than the impedance of one of the two opposing coils forming each of the at least one pair. Accordingly, an electrical current that generates the second magnetic field flows in the at least one pair, but does not flow in the element. Thus, the at least one pair of opposing coils can generate the second magnetic field.

According to the fourth aspect of the present invention, it is desirable that at least three pairs of opposing coils are disposed around an area where the at least one magnet is disposed, the first magnetic field generating unit includes a magnetic field generating coil disposed in the vicinity of one of the opposing coils forming at least one pair, the position detecting means includes a magnetic field sensor disposed in the vicinity of the other opposing coil forming the at least one pair, and the direction of a center axis of at least one pair among the at least three pairs of opposing coils crosses a plane formed by center axes of the other two pairs of opposing coils.

In such a configuration, the magnetic field generating coil generates the first magnetic field that induces an induction magnetic field of the internal coil included in the medical device. The induction magnetic field emanating from the internal coil is detected by the magnetic field sensor and is used for detecting the position and the attitude of the medical device including the internal coil. Additionally, the second magnetic field generated by the at least three pairs of opposing coils acts on the magnet included in the medical device so as to control the position and the attitude of the medical device. Here, since the direction of a center axis of at least one pair among the at least three pairs of opposing coils crosses a plane formed by center axes of the other two pair of opposing coils, the magnetic field lines of the second magnetic field can be three-dimensionally directed in any direction. Thus, the position or the attitude of the medical device including the magnet can be three-dimensionally controlled.

In addition, even when the condition under which mutual induction due to the first magnetic field emanating from the magnetic field generating coil disposed in the vicinity of one of the opposing coils is induced in the one of the opposing coils occurs, at least the other one of the opposing coils produces only the second magnetic field without producing a magnetic field having a phase that is the same as that of the mutual induction magnetic field having a reversed phase to that of the first magnetic field. As a result, since the other one of the opposing coils does not produce a magnetic field that cancels out the first magnetic field, formation of an area where the first magnetic field is substantially zero can be prevented.

In a medical-device magnetic guiding and position detecting system according to the present invention, even when the condition under which mutual induction is induced in one of the opposing coils occurs, at least the other opposing coil can prevent the occurrence of a mutual induction magnetic field. Thus, an area where the first magnetic field is canceled out and the strength of the first magnetic field is substantially zero is not formed. As a result, a decrease in the strength of a position detecting magnetic field can be prevented.

BRIEF DESCRIPTION OF THE SEVERAL VIEWS OF THE DRAWINGS

FIG. 20 is a block diagram illustrating a schematic configuration of guiding magnetic field generating coils shown in FIG. 19; and FIG. 21 is a diagram illustrating the strength of a magnetic field generated by a known medical-device magnetic guiding and position detecting system.

DETAILED DESCRIPTION OF THE INVENTION

First Embodiment

A medical-device magnetic guiding and position detecting system according to a first embodiment of the present invention is described below with reference to FIGS. 1 to 4.

Figure 1:
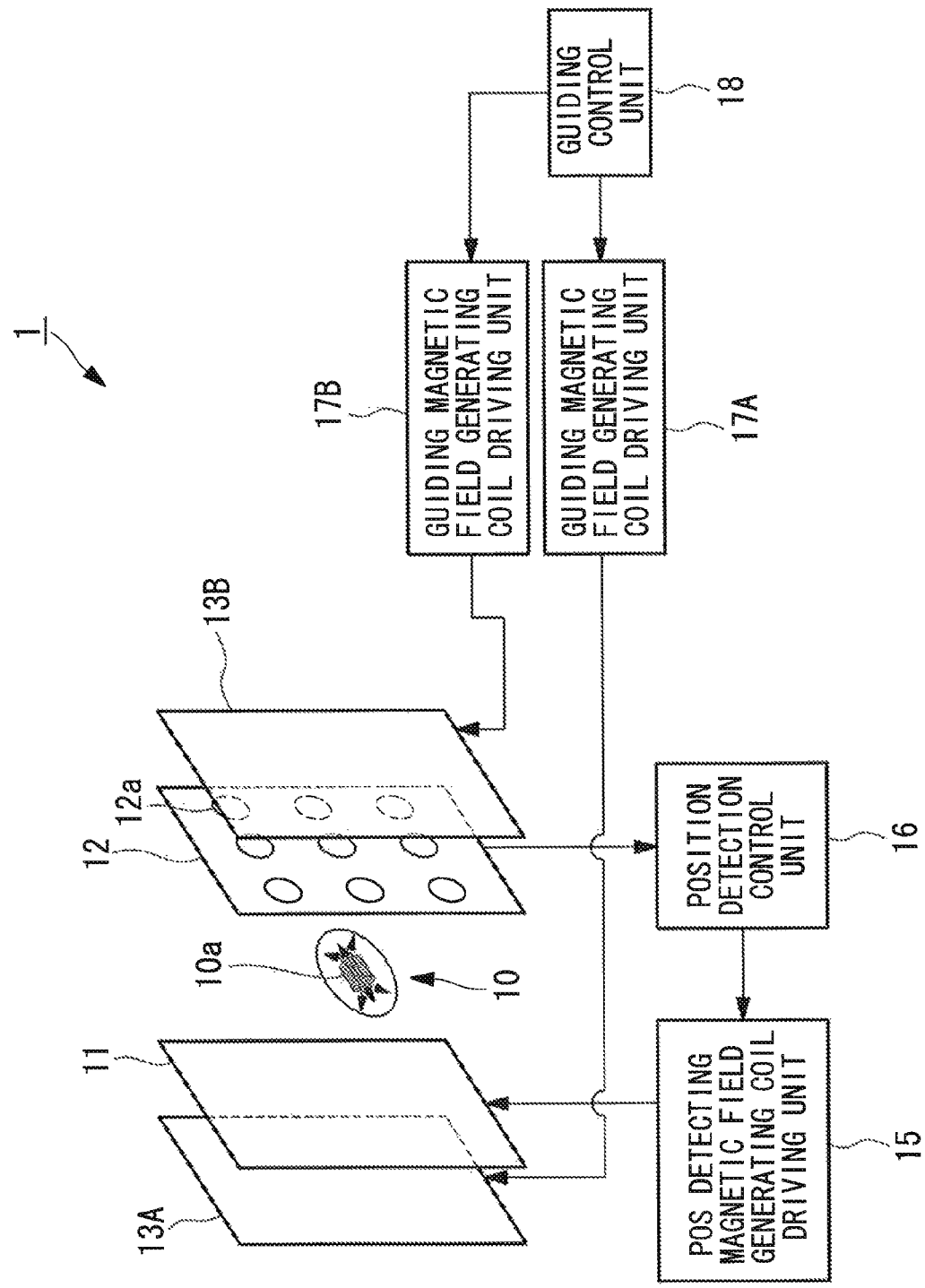
FIG. 1 is a block diagram of the schematic configuration of a medical-device magnetic guiding and position detecting system according to a first embodiment of the present invention.

FIG. 1 is a block diagram of the schematic configuration of the medical-device magnetic guiding and position detecting system according to the present embodiment.

As shown in FIG. 1, a medical-device magnetic guiding and position detecting system 1 includes a position detecting magnetic field generating coil (a first magnetic field generating unit) 11 for generating a position detecting magnetic field (a first magnetic field), a magnetic field sensor (position detecting means) 12 for detecting an induced magnetic field emanating from an internal coil 10a mounted in a capsule medical device (medical device) 10, and guiding magnetic field generating coils (opposing coils) 13A and 13B for generating a guiding magnetic field (a second magnetic field) for guiding the capsule medical device to a predetermined location in a body cavity.

The capsule medical device 10 includes a closed circuit including the internal coil 10a and a capacitor having a predetermined capacitance and a magnet (not shown) used for controlling the position and attitude of the capsule medical device 10 in response to the guiding magnetic field. The closed circuit forms an LC resonant circuit that resonates at a predetermined frequency. Although the closed circuit is formed as an LC resonant circuit, the closed circuit can be equivalently formed by only the internal coil 10a having either end open if the parasitic capacitance of the internal coil 10a can realize the predetermined resonance frequency.

Examples of the capsule medical device 10 include a variety of medical devices, including but not limited to, an endoscopic capsule having an electronic image pickup device, such as a CCD or a CMOS, and a medical device for carrying medicine to a predetermined location in a body cavity of a subject and releasing the medicine at that location.

The position detecting magnetic field generating coil 11 is composed of a substantially flat coil. The position detecting magnetic field generating coil 11 is electrically connected to a position detecting magnetic field generating coil driving unit 15.

The magnetic field sensor 12 includes a plurality of detection coils 12a disposed substantially on a plane. Each of the detection coils 12a is electrically connected to a position detection control unit 16. The output of each detection coil 12a is input to the position detection control unit 16.

The position detection control unit 16 is electrically connected to the position detecting magnetic field generating coil driving unit 15. A control signal generated by the position detection control unit 16 is input to the position detecting magnetic field generating coil driving unit 15.

Figure 2:
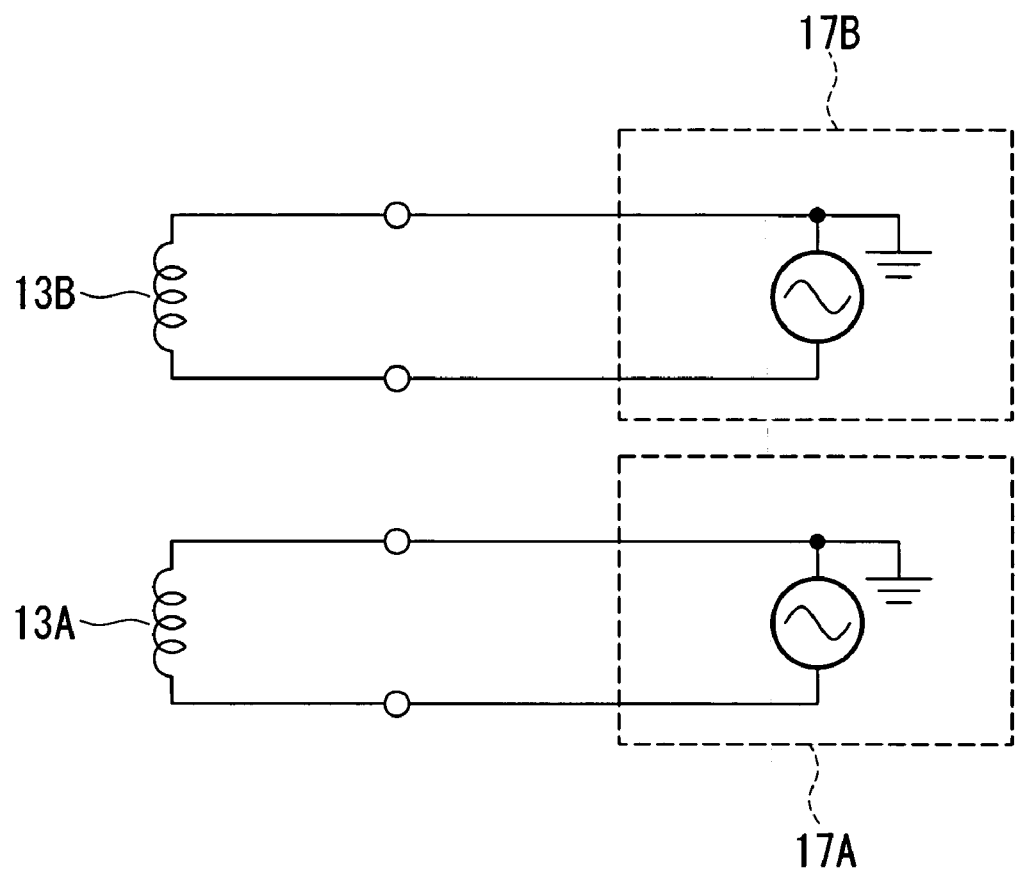
FIG. 2 is a connection diagram illustrating the configuration of a guiding magnetic field generating coil shown in FIG. 1.

FIG. 2 is a connection diagram illustrating the configuration of the guiding magnetic field generating coil shown in FIG. 1.

Each of the guiding magnetic field generating coils 13A and 13B is composed of a substantially flat coil. As shown in FIGS. 1 and 2, the guiding magnetic field generating coils 13A and 13B are electrically connected to guiding magnetic field generating coil driving units 17A and 17B, respectively. The guiding magnetic field generating coil driving units 17A and 17B are electrically connected to a guiding control unit 18 so as to receive a control signal generated by the guiding control unit 18.

The guiding magnetic field generating coil 13A is disposed in the vicinity of the position detecting magnetic field generating coil 11 so as to face the position detecting magnetic field generating coil 11. In addition, the guiding magnetic field generating coil 13A is disposed on the opposite side of the position detecting magnetic field generating coil 11 from the capsule medical device 10. The guiding magnetic field generating coil 13B is disposed in the vicinity of the magnetic field sensor 12 so as to face the magnetic field sensor 12. In addition, the guiding magnetic field generating coil 13B is disposed on the opposite side of the magnetic field sensor 12 from the capsule medical device 10.

Figure 3:
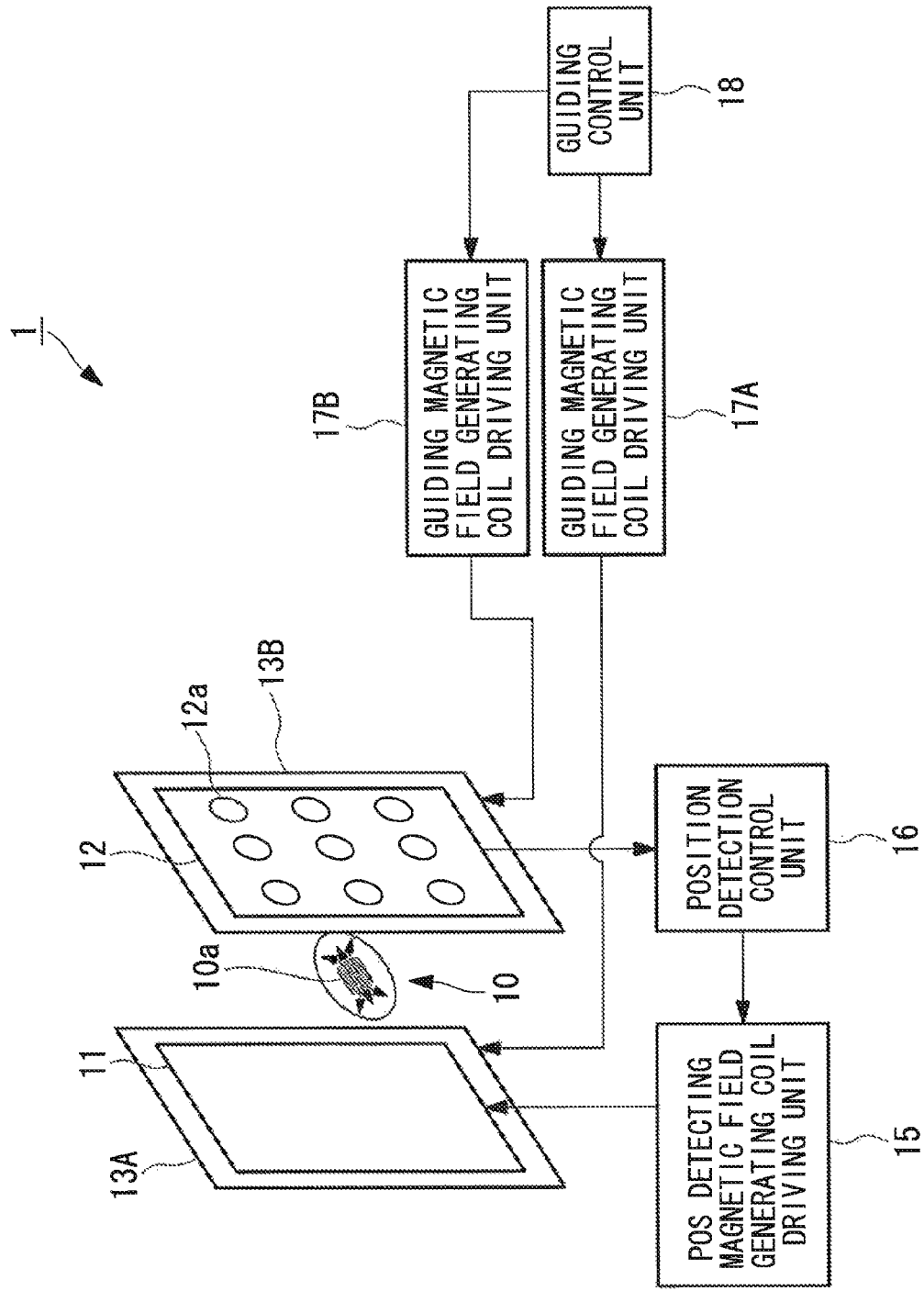
FIG. 3 is a block diagram of the medical-device magnetic guiding and position detecting system shown in FIG. 1 according to another embodiment of the present invention.

Note that the positions of the guiding magnetic field generating coil 13A and the position detecting magnetic field generating coil 11 are interchangeable. Alternatively, the positions of the guiding magnetic field generating coil 13B and the magnetic field sensor 12 are interchangeable. In addition, when the guiding magnetic field generating coil 13A has a hollow core and the position detecting magnetic field generating coil 11 can be disposed inside the core of the guiding magnetic field generating coil 13A, the guiding magnetic field generating coil 13A and the position detecting magnetic field generating coil 11 may be disposed on substantially the same plane, as shown in FIG. 3. Additionally, when the guiding magnetic field generating coil 13B has a hollow core and the magnetic field sensor 12 can be disposed inside the core of the guiding magnetic field generating coil 13B, the guiding magnetic field generating coil 13B and the magnetic field sensor 12 may be disposed on substantially the same plane.

The operation of the medical-device magnetic guiding and position detecting system 1 having such a configuration is described next.

As shown in FIG. 1, the position detection control unit 16 generates a position detection control signal which is an alternating current signal having a predetermined frequency. The position detection control signal is output to the position detecting magnetic field generating coil driving unit 15. The position detecting magnetic field generating coil driving unit 15 amplifies the input position detection control signal to a predetermined strength so as to generate a driving electrical current for driving the position detecting magnetic field generating coil 11. Upon receiving the driving electrical current, the position detecting magnetic field generating coil 11 forms a position detecting magnetic field therearound.

When magnetic fluxes of the position detecting magnetic field pass through the capsule medical device 10, the closed circuit having the internal coil 10a in the capsule medical device 10 induces a resonant electrical current at a predetermined frequency. When the resonant electrical current is induced in the closed circuit, the internal coil 10a forms an induced magnetic field having a predetermined frequency therearound due to the resonant electrical current.

Since a magnetic flux of the position detecting magnetic field and a magnetic flux of the induced magnetic field pass through the detection coils 12a of the magnetic field sensor 12, the detection coils 12a picks up the sum of the two magnetic fluxes and generates an output signal which is an induced electrical current on the basis of the change in the passing magnetic fluxes. The output signal is delivered from the detection coils 12a to the position detection control unit 16.

The position detection control unit 16 controls the frequency of the position detecting magnetic field generated by the position detecting magnetic field generating coil 11. More specifically, the position detection control unit 16 changes the frequency of the generating control signal so as to change the frequency of the position detecting magnetic field. When the frequency of the position detecting magnetic field is changed, the relationship between the frequency of the position detecting magnetic field and the resonance frequency of the closed circuit of the capsule medical device 10 is changed. Thus, the strength of the induced magnetic field formed by the internal coil 10a is changed. In this example, the change in a detection voltage at about the resonance frequency is detected in order to use the change for computing the position.

In addition, the position detection control unit 16 estimates the position of the internal coil 10a, i.e., the position of the capsule medical device 10 on the basis of the output signal from the detection coils 12a using a known computation method.

As shown in FIGS. 1 and 2, the guiding control unit 18 generates the guiding control signal, which is an alternating current signal having a predetermined frequency, and outputs the guiding control signal to the guiding magnetic field generating coil driving units 17A and 17B.

The guiding magnetic field generating coil driving units 17A and 17B amplify the input guiding control signal to a predetermined strength so as to generate a driving current for driving the guiding magnetic field generating coils 13A and 13B. The driving current is output to the guiding magnetic field generating coils 13A and 13B. Upon receiving the driving current, the guiding magnetic field generating coils 13A and 13B form a guiding magnetic field therearound.

Since the guiding magnetic field generating coils are connected to the guiding magnetic field generating coil driving units having a significantly low output impedance, mutual induction occurs between the two coils when the position detecting magnetic field passes through the guiding magnetic field generating coils. The mutual induction generates an electromotive force, which applies an electrical current to a closed circuit formed by the guiding magnetic field generating coils and the guiding magnetic field generating coil driving units. Therefore, the guiding magnetic field generating coils produce a magnetic field that cancels out the position detecting magnetic field.

Figure 4:
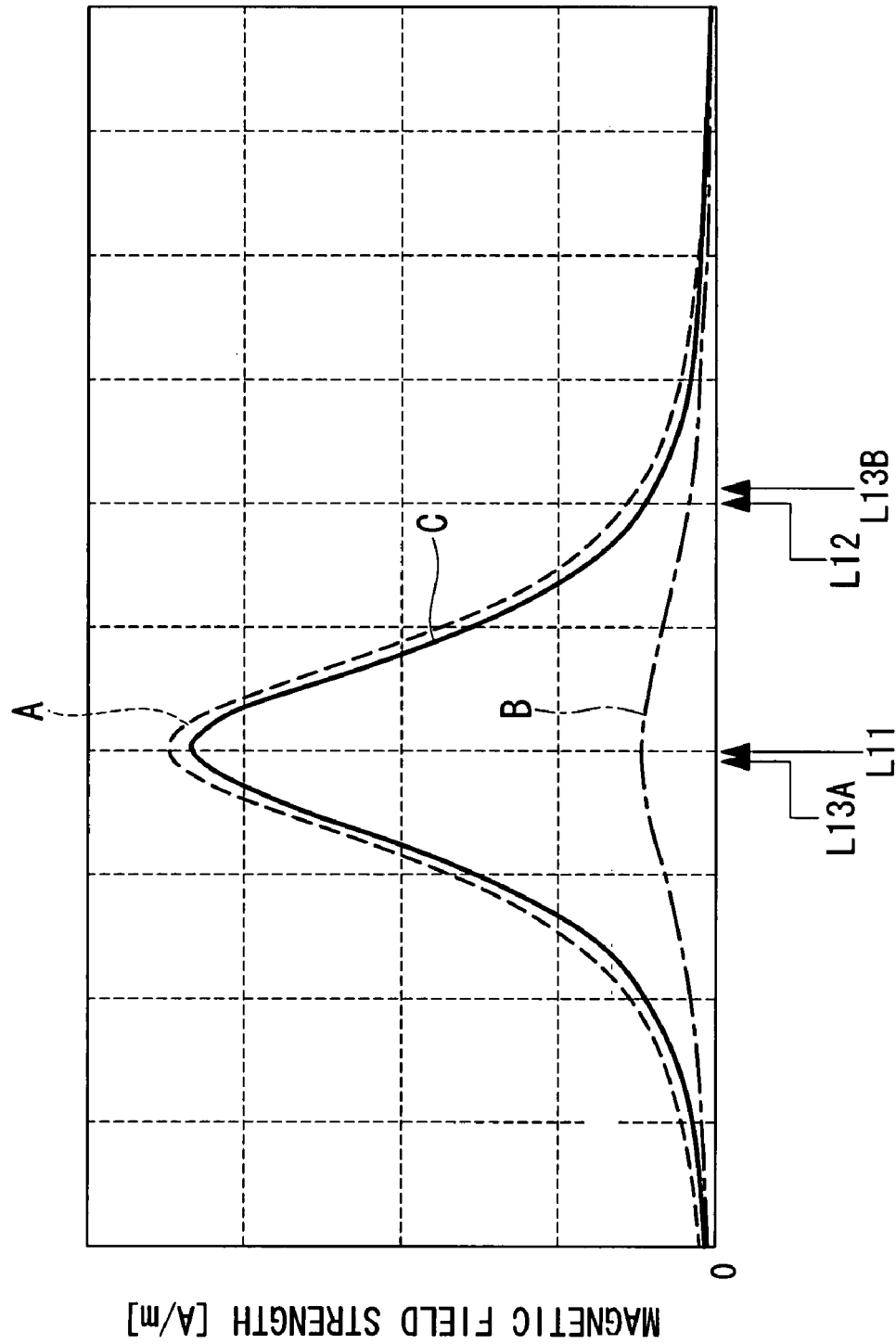
FIG. 4 illustrates the strength of a magnetic field generated by the medical-device magnetic guiding and position detecting system shown in FIG. 1.

FIG. 4 illustrates the strength of a magnetic field generated by the medical-device magnetic guiding and position detecting system shown in FIG. 1.

The above-described position detecting magnetic field generating coil 11 and the guiding magnetic field generating coils 13A and 13B generate magnetic fields having a magnetic field strength distribution shown in FIG. 4. In FIG. 4, the strength distribution of the position detecting magnetic field produced by the position detecting magnetic field generating coil 11 is shown by a dotted line A. The strength distribution of the mutual induction magnetic field produced by the guiding magnetic field generating coil 13A is shown by an alternate long and short dash line B. A combined magnetic field composed of the position detecting magnetic field and the mutual induction magnetic field emanating from the guiding magnetic field generating coils is shown by a solid line C.

The strength distribution indicates that the position detecting magnetic field is maximized at a position L11 at which the position detecting magnetic field generating coil 11 is disposed, and the strength of the position detecting magnetic field decreases in a direction away from the position L11. In addition, the strength distribution indicates that the mutual induction magnetic field emanating from the guiding magnetic field generating coils is maximized at a position L13A at which the guiding magnetic field generating coil 13A is disposed, and the strength of the mutual induction magnetic field decreases in a direction away from the position L11. Furthermore, since the position detecting magnetic field and the mutual induction magnetic field have the substantially opposite phases, the combined magnetic field composed of the position detecting magnetic field and the mutual induction magnetic field cancel each other out.

Here, the position L13A at which the strength of the mutual induction magnetic field is maximized is located in the vicinity of the position L11 or exactly at the position L11 at which the strength of the position detecting magnetic field is maximized. The maximum strength of the mutual induction magnetic field is lower than the maximum strength of the position detecting magnetic field. Accordingly, the strength of the mutual induction magnetic field is not substantially equal to the strength of the position detecting magnetic field or is not higher than the strength of the position detecting magnetic field at least in a space between the guiding magnetic field generating coils 13A and 13B. Consequently, the combined magnetic field exhibits a magnetic field strength distribution weaker than the strength of the position detecting magnetic field. The combined magnetic field is maximized in the vicinities of the position L11 at which the position detecting magnetic field generating coil 11 is disposed and the position L13A at which the position L13A is disposed. In addition, the strength distribution indicates that the strength of the combined magnetic field decreases in a direction away from the position L11 or the position L13A.

In the above-described configuration, as shown in FIG. 21, an area where the combined magnetic field is substantially zero is not formed. Accordingly, an area where an induction magnetic field is not generated is not formed for the internal coil 10a mounted in the capsule medical device 10. As a result, an area where the position of the capsule medical device 10 cannot be detected is not formed.

The guiding magnetic field generating coils 13A and 13B are independently driven by the guiding magnetic field generating coil driving units 17A and 17B, respectively. Accordingly, when the guiding magnetic field generating coil driving unit 17B drives and controls the guiding magnetic field generating coil 13B, an electrical current caused by an electromotive force generated in the guiding magnetic field generating coil 13A does not flow in the guiding magnetic field generating coil 13B. As a result, a magnetic field that significantly cancels out the position detecting magnetic field is not produced in the vicinity of the magnetic field sensor.

In addition, the guiding magnetic field can be continuously generated by the guiding magnetic field generating coil driving unit 17A driving and controlling the guiding magnetic field generating coil 13A. Therefore, the capsule medical device 10 can be continuously guided.

Second Embodiment

A second embodiment of the present invention is described next with reference to FIGS. 5 to 7.

The basic configuration of the medical-device magnetic guiding and position detecting system according to the present embodiment is similar to that of the first embodiment except for the structure of a guiding magnetic field generating coil driving unit. Therefore, according to the present embodiment, only the structure and related components of the guiding magnetic field generating coil driving unit are described next with reference to FIGS. 5 to 7. Descriptions of the other components are not repeated.

Figure 5:
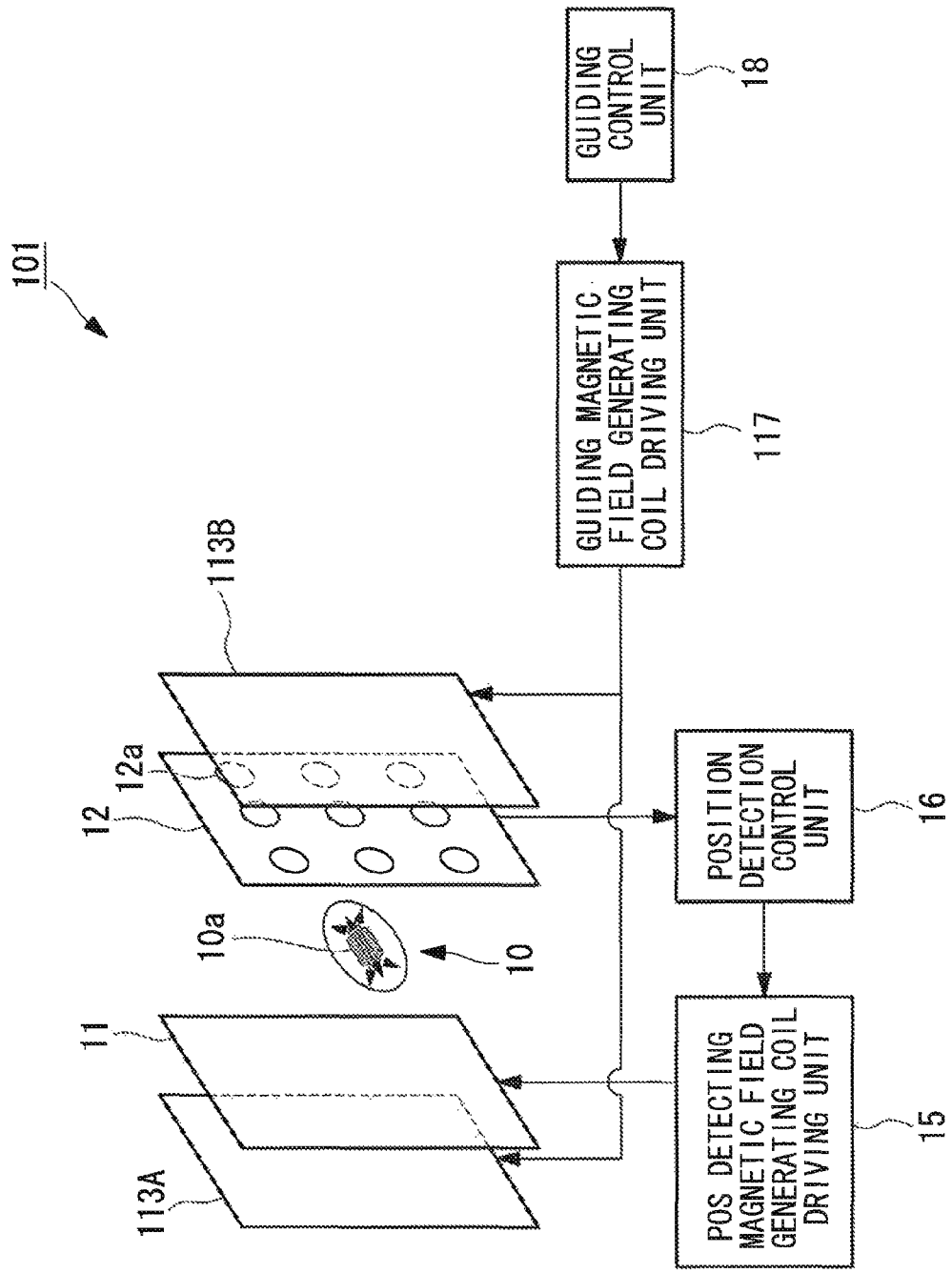
FIG. 5 is a block diagram of the schematic configuration of a medical-device magnetic guiding and position detecting system according to a second embodiment of the present invention.

FIG. 5 is a block diagram of the medical-device magnetic guiding and position detecting system according to the present embodiment.

In FIG. 5, the same components as those illustrated and described in relation to the first embodiment are designated by the same reference numerals. Descriptions of these components are not repeated here.

As shown in FIG. 5, a medical-device magnetic guiding and position detecting system 101 includes a position detecting magnetic field generating coil 11 for generating a position detecting magnetic field, a magnetic field sensor 12 for detecting an induced magnetic field generated by an internal coil 10a mounted in a capsule medical device 10, and guiding magnetic field generating coils (opposing coils) 113A and 113B for generating a guiding magnetic field.

Figure 6:
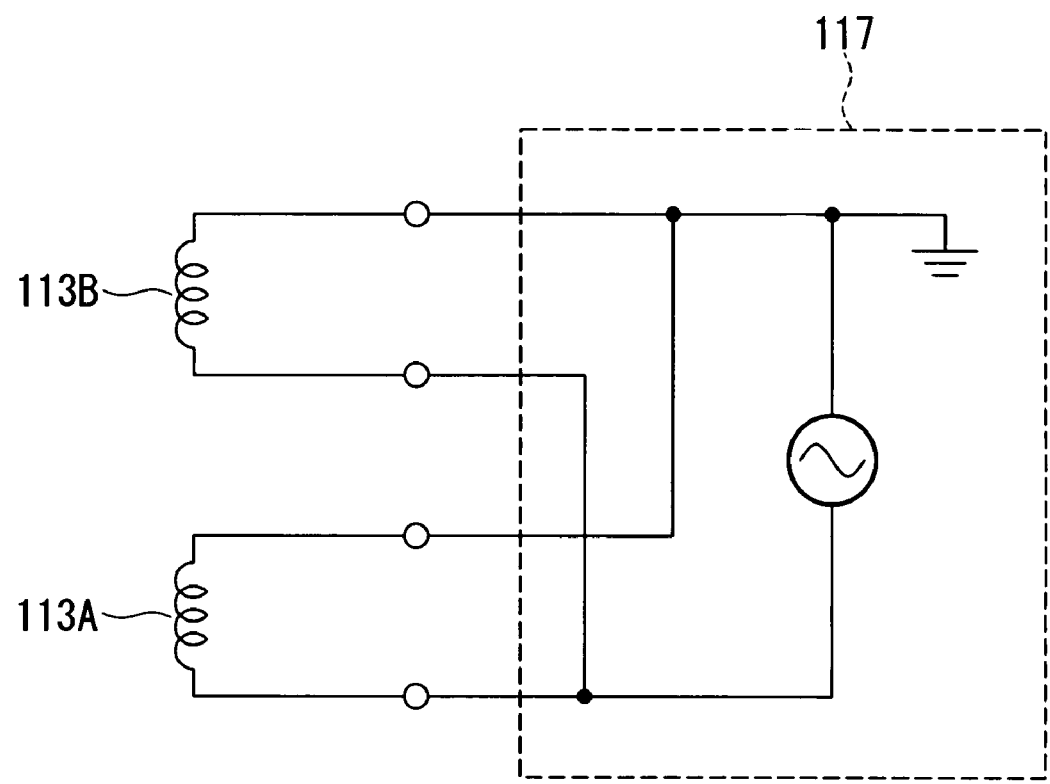
FIG. 6 is a connection diagram illustrating the configuration of a guiding magnetic field generating coil shown in FIG. 5.
Figure 7:
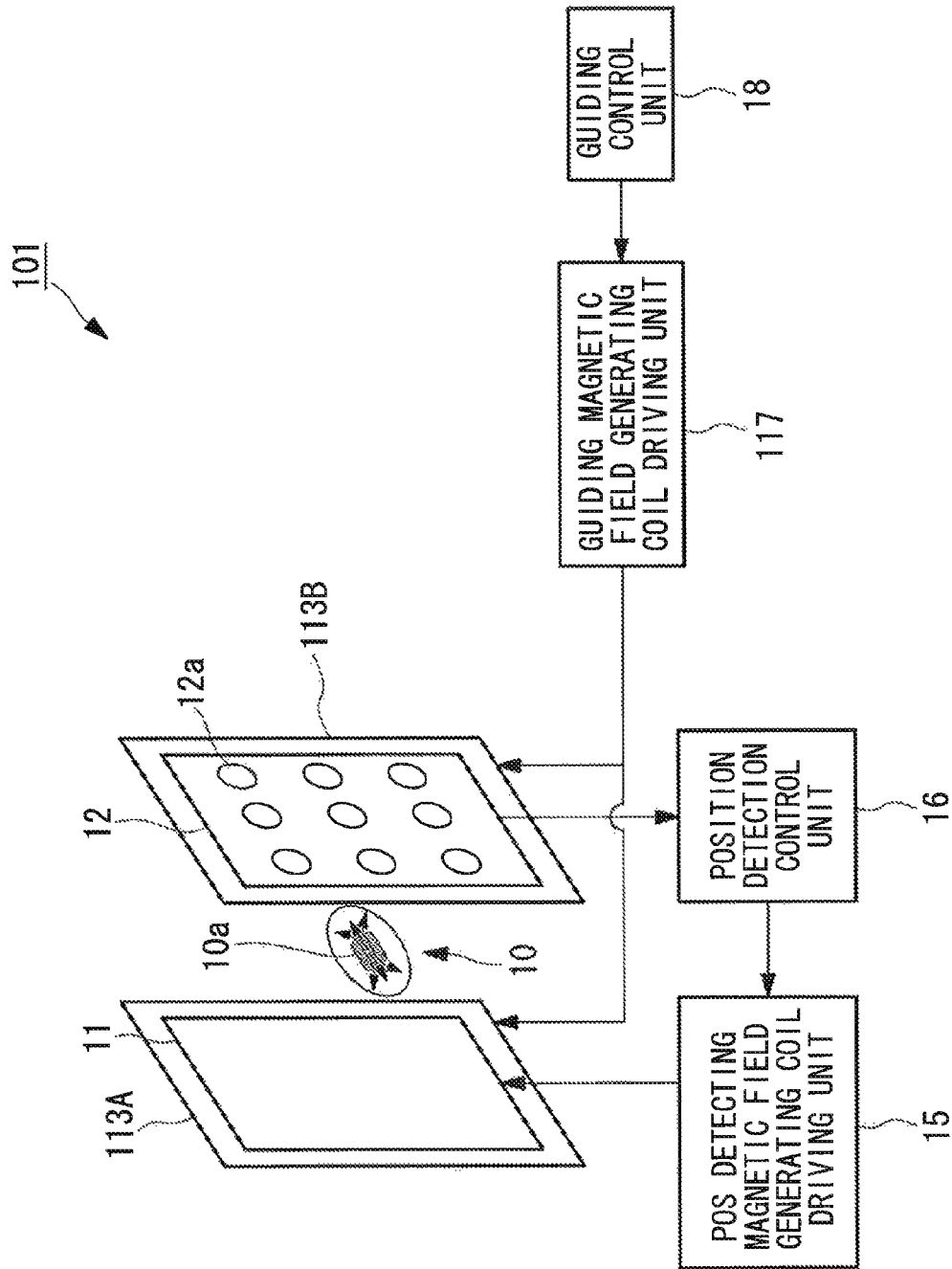
FIG. 7 is a block diagram of the medical-device magnetic guiding and position detecting system shown in FIG. 5 according to another embodiment of the present invention.

FIG. 6 is a connection diagram illustrating the configuration of the guiding magnetic field generating coil shown in FIG. 5.

Each of the guiding magnetic field generating coils 113A and 113B is composed of a substantially flat coil. As shown in FIGS. 5 and 6, the guiding magnetic field generating coils 113A and 113B are electrically connected to a guiding magnetic field generating coil driving unit 117. The guiding magnetic field generating coils 113A and 113B are electrically connected to the guiding magnetic field generating coil driving unit 117 in parallel. The guiding magnetic field generating coil driving unit 117 is electrically connected to a guiding control unit 18 so as to receive a control signal generated by the guiding control unit 18.

The guiding magnetic field generating coil 113A is disposed in the vicinity of the position detecting magnetic field generating coil 11 so as to face the position detecting magnetic field generating coil 11. In addition, the guiding magnetic field generating coil 113A is disposed on the opposite side of the position detecting magnetic field generating coil 11 from the capsule medical device 10. The guiding magnetic field generating coil 113B is disposed in the vicinity of the magnetic field sensor 12 so as to face the magnetic field sensor 12. In addition, the guiding magnetic field generating coil 113B is disposed on the opposite side of the magnetic field sensor 12 from the capsule medical device 10.

Note that the positions of the guiding magnetic field generating coil 113A and the position detecting magnetic field generating coil 11 are interchangeable. Alternatively, the positions of the guiding magnetic field generating coil 113B and the magnetic field sensor 12 are interchangeable. In addition, when the guiding magnetic field generating coil 113A has a hollow core and the position detecting magnetic field generating coil 11 can be disposed inside the core of the guiding magnetic field generating coil 113A, the guiding magnetic field generating coil 113A and the position detecting magnetic field generating coil 11 may be disposed on substantially the same plane, as shown in FIG. 7. Additionally, when the guiding magnetic field generating coil 113B has a hollow core and the magnetic field sensor 12 can be disposed inside the core of the guiding magnetic field generating coil 113B, the guiding magnetic field generating coil 113B and the magnetic field sensor 12 may be disposed on substantially the same plane.

The operation of the medical-device magnetic guiding and position detecting system 101 having such a configuration is described next.

The operation of the medical-device magnetic guiding and position detecting system 101 for detecting the position of the capsule medical device 10, such as formation of a position detecting magnetic field by the position detecting magnetic field generating coil 11 and the formation of an induction magnetic field by the internal coil 10a, is similar to that of the first embodiment, and therefore, description thereof is not repeated here.

As shown in FIGS. 5 and 6, the guiding control unit 18 generates a guiding control signal which is an alternating current signal having a predetermined frequency. The guiding control signal is output to the guiding magnetic field generating coil driving unit 117.

The guiding magnetic field generating coil driving unit 117 amplifies the input guiding control signal to a predetermined strength so as to generate a driving electrical current for driving the guiding magnetic field generating coils 113A and 113B. The driving electrical current is output to the guiding magnetic field generating coils 113A and 113B. Upon receiving the driving electrical current, the guiding magnetic field generating coils 113A and 113B form guiding magnetic fields therearound.

The strength distributions of the position detecting magnetic field formed by the position detecting magnetic field generating coil 11, a mutual induction magnetic field emanating from the guiding magnetic field generating coil, and combined magnetic field composed of these magnetic fields are similar to those described in the first embodiment, and therefore, descriptions thereof are not repeated here.

In the above-described configuration, an area where the combined magnetic field is substantially zero is not formed. Accordingly, an area where the induction magnetic field is not generated is not formed for the internal coil 10a mounted in the capsule medical device 10. As a result, an area where the position of the capsule medical device 10 cannot be detected is not formed.

Since the guiding magnetic field generating coils 113A and 113B are electrically connected in parallel, the position detecting magnetic field does not generate a mutual induction magnetic field in the guiding magnetic field generating coil 113B.

In addition, since the guiding magnetic field generating coil 113B can continuously generate the guiding magnetic field, the capsule medical device 10 can be continuously guided.

Third Embodiment

A third embodiment of the present invention is described next with reference to FIGS. 8 to 10.

The basic configuration of the medical-device magnetic guiding and position detecting system according to the present embodiment is similar to that of the first embodiment except for the structure of a guiding magnetic field generating coil driving unit. Therefore, according to the present embodiment, only the structure and related components of the guiding magnetic field generating coil driving unit are described next with reference to FIGS. 8 to 10. Descriptions of the other components are not repeated.

Figure 8:
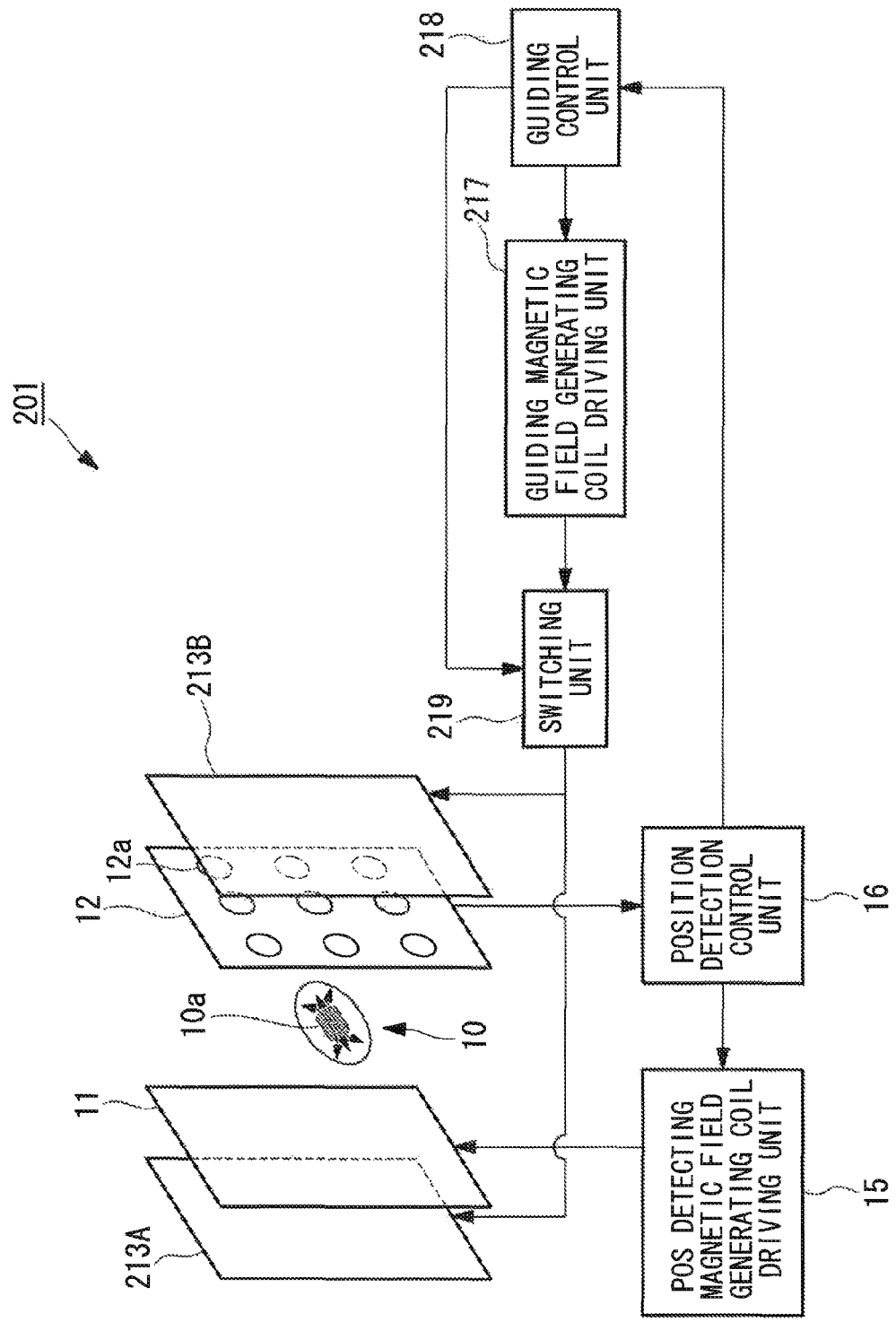
FIG. 8 is a block diagram of the schematic configuration of a medical-device magnetic guiding and position detecting system according to a third embodiment of the present invention.

FIG. 8 is a block diagram of the medical-device magnetic guiding and position detecting system according to the present embodiment.

In FIG. 8, the same components as those illustrated and described in relation to the first embodiment are designated by the same reference numerals. Descriptions of these components are not repeated here.

As shown in FIG. 8, a medical-device magnetic guiding and position detecting system 201 includes a position detecting magnetic field generating coil 11 for generating a position detecting magnetic field, a magnetic field sensor 12 for detecting an induced magnetic field generated by an internal coil 10a mounted in a capsule medical device 10, and guiding magnetic field generating coils (opposing coils) 213A and 213B for generating a guiding magnetic field.

Figure 9:
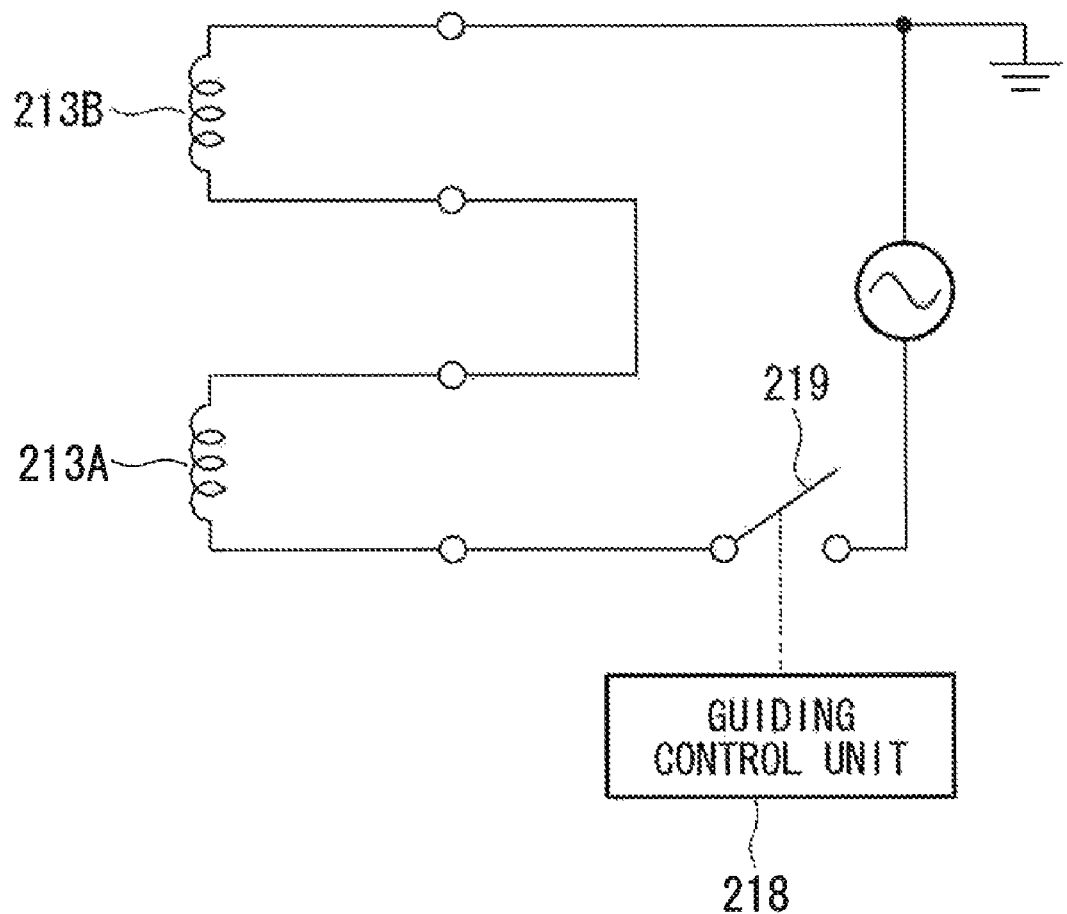
FIG. 9 is a connection diagram illustrating the configuration of a guiding magnetic field generating coil shown in FIG. 8.
Figure 10:
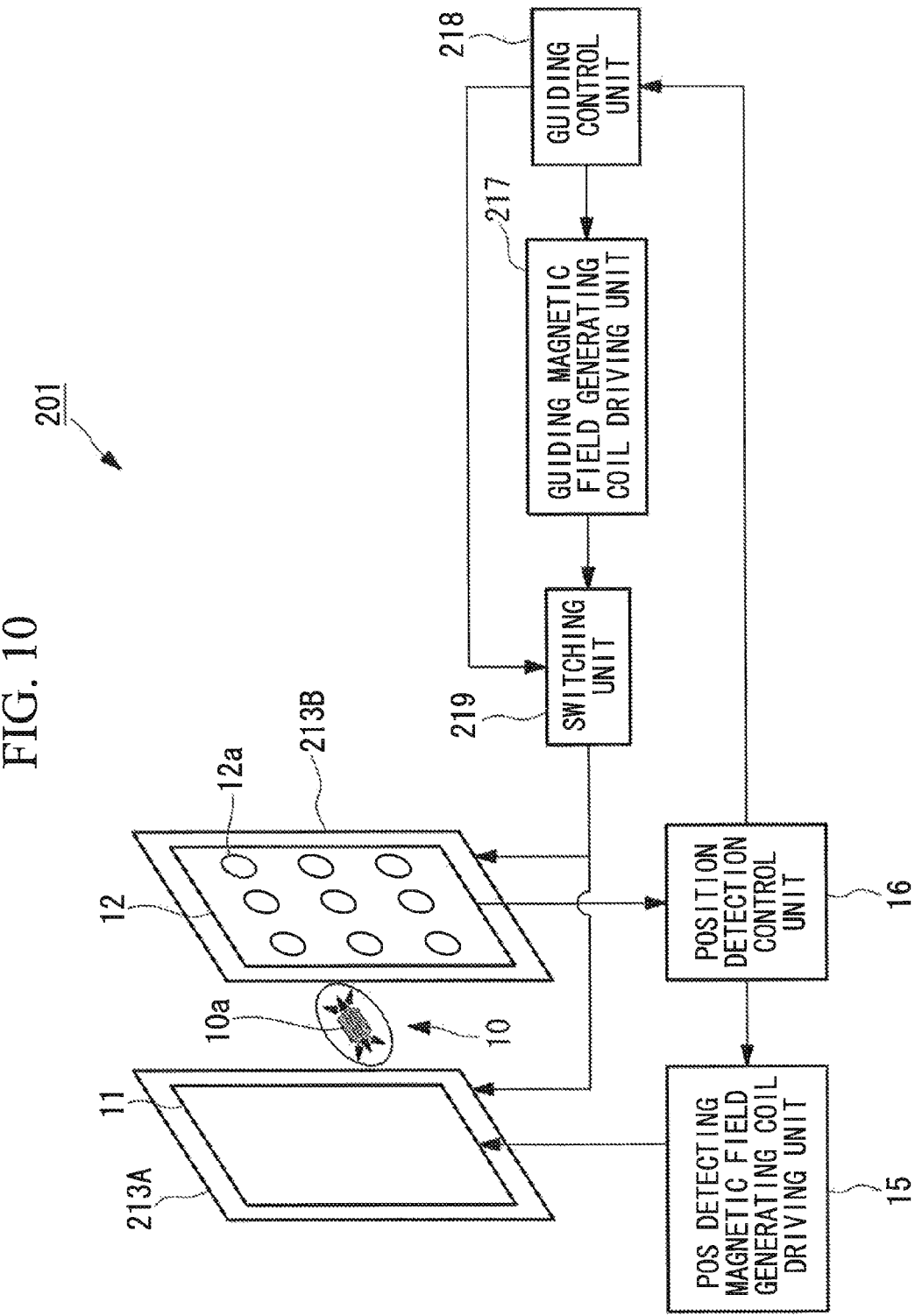
FIG. 10 is a block diagram of the medical-device magnetic guiding and position detecting system shown in FIG. 8 according to another embodiment of the present invention.

FIG. 9 is a connection diagram illustrating the structure of the guiding magnetic field generating coil shown in FIG. 8.

Each of the guiding magnetic field generating coils 213A and 213B is composed of a substantially flat coil. As shown in FIGS. 8 and 9, the guiding magnetic field generating coils 213A and 213B are electrically connected to a guiding magnetic field generating coil driving unit 217 via a switching unit 219. The switching unit 219 is provided in a closed circuit formed by the guiding magnetic field generating coils 213A and 213B and the guiding magnetic field generating coil driving unit 217.

The guiding magnetic field generating coils 213A and 213B are electrically connected in series. The guiding magnetic field generating coil driving unit 217 is electrically connected to a guiding control unit 218 and receives a control signal generated by the guiding control unit 218. The guiding control unit 218 is electrically connected to the switching unit 219. An ON/OFF signal generated by the guiding control unit 218 is input to the switching-unit 219. Additionally, the guiding control unit 218 is electrically connected to the position detection control unit 16 and receives an operation signal output from the position detection control unit 16.

The guiding magnetic field generating coil 213A is disposed in the vicinity of the position detecting magnetic field generating coil 11 so as to face the position detecting magnetic field generating coil 11. In addition, the guiding magnetic field generating coil 213A is disposed on the opposite side of the position detecting magnetic field generating coil 11 from the capsule medical device 10. The guiding magnetic field generating coil 213B is disposed in the vicinity of the magnetic field sensor 12 so as to face the magnetic field sensor 12. In addition, the guiding magnetic field generating coil 213B is disposed on the opposite side of the magnetic field sensor 12 from the capsule medical device 10.

Note that the positions of the guiding magnetic field generating coil 213A and the position detecting magnetic field generating coil 11 are interchangeable. Alternatively, the positions of the guiding magnetic field generating coil 213B and the magnetic field sensor 12 are interchangeable. In addition, when the guiding magnetic field generating coil 213A has a hollow core and the position detecting magnetic field generating coil 11 can be disposed inside the core of the guiding magnetic field generating coil 213A, the guiding magnetic field generating coil 213A and the position detecting magnetic field generating coil 11 may be disposed on substantially the same plane, as shown in FIG. 10. Additionally, when the guiding magnetic field generating coil 213B has a hollow core and the magnetic field sensor 12 can be disposed inside the core of the guiding magnetic field generating coil 213B, the guiding magnetic field generating coil 213B and the magnetic field sensor 12 may be disposed on substantially the same plane.

The operation of the medical-device magnetic guiding and position detecting system 201 having such a configuration is described next.

The operation of the medical-device magnetic guiding and position detecting system 201 for detecting the position of the capsule medical device 10, such as formation of a position detecting magnetic field by the position detecting magnetic field generating coil 11 and the formation of an induction magnetic field by the internal coil 10a, is similar to that of the first embodiment, and therefore, description thereof is not repeated here.

As shown in FIGS. 8 and 9, the guiding control unit 218 generates a guiding control signal which is an alternating current signal having a predetermined frequency. The guiding control signal is output to the guiding magnetic field generating coil driving units 217.

The guiding magnetic field generating coil driving units 217 amplifies the input guiding control signal to a predetermined strength so as to generate a driving electrical current for driving the guiding magnetic field generating coils 213A and 213B. The driving electrical current is output to the guiding magnetic field generating coils 213A and 213B. Upon receiving the driving electrical current, the guiding magnetic field generating coils 213A and 213B form guiding magnetic fields therearound.

The guiding control unit 218 outputs an ON/OFF signal for controlling the switching unit 219 on the basis of the operation signal input from the position detection control unit 16. The operation signal is generated on the basis of a control signal output to the position detecting magnetic field generating coil driving unit 15. That is, while the control signal for generating the position detecting magnetic field is being output to the position detecting magnetic field generating coil driving unit 15, the operation signal for turning off (opening)

the switching unit 219 is being output. In contrast, while the control signal is not being output to the position detecting magnetic field generating coil driving unit 15, the operation signal for turning on (closing) the switching unit 219 is being output.

In this way, the guiding control unit 218 outputs the ON/OFF signal to the switching unit 219 on the basis of the input control signal. The switching unit 219 performs ON/OFF control on the basis of the ON/OFF signal.

To turn on or off the switching unit 219, the switching unit 219 may be simply on-off controlled, as described above. Alternatively, the guiding control unit 218 may gradually change the amplitude of a signal input to the guiding magnetic field generating coil driving unit 217 on the basis of the operation signal. This control method can prevent the guiding magnetic field generating coil driving unit 217 from being damaged by a back electromotive force caused by self-induction of the guiding magnetic field generating coils 213A and 213B.

Alternatively, to turn off the switching unit 219, the guiding control unit 218 may gradually decrease the amplitude of a signal input to the guiding magnetic field generating coil driving unit 217 to zero on the basis of the operation signal. When the amplitude of the input signal reaches zero, the switching unit 219 may be turned off.

In such a configuration, the position detecting magnetic field generating coil 11 and the guiding magnetic field generating coils 213A and 213B can be driven in a time-multiplexing manner. Accordingly, the occurrence of mutual induction between the position detecting magnetic field generating coil 11 and the guiding magnetic field generating coils 213A and 213B can be prevented. Thus, an area where the strength of the combined magnetic field composed of the position detecting magnetic field and the mutual induction magnetic field emanating from the guiding magnetic field generating coil is substantially zero is not formed. As a result, a decrease in the strength of the position detecting magnetic field in an operating area of the capsule medical device 10 can be prevented.

Fourth Embodiment

A fourth embodiment of the present invention is described next with reference to FIGS. 11 to 13.

The basic configuration of the medical-device magnetic guiding and position detecting system according to the present embodiment is similar to that of the first embodiment except for the structure of a guiding magnetic field generating coil driving unit. Therefore, according to the present embodiment, only the structure and related components of the guiding magnetic field generating coil driving unit are described next with reference to FIGS. 11 to 13. Descriptions of the other components are not repeated.

Figure 11:
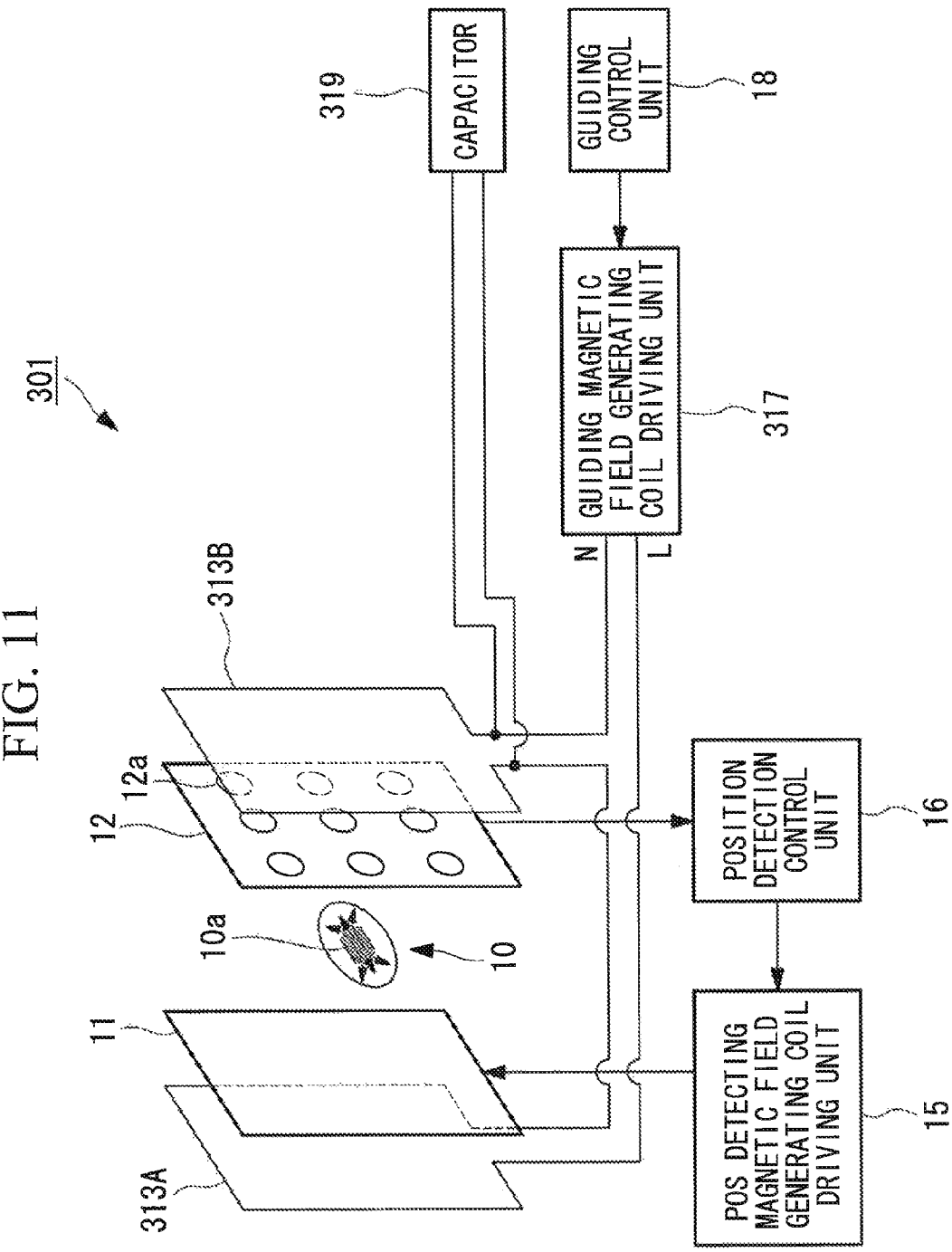
FIG. 11 is a block diagram of the schematic configuration of a medical-device magnetic guiding and position detecting system according to a fourth embodiment of the present invention.

FIG. 11 is a block diagram of the medical-device magnetic guiding and position detecting system according to the present embodiment.

In FIG. 11, the same components as those illustrated and described in relation to the first embodiment are designated by the same reference numerals. Descriptions of these components are not repeated here.

As shown in FIG. 11, a medical-device magnetic guiding and position detecting system 301 includes a position detecting magnetic field generating coil 11 for generating a position detecting magnetic field, a magnetic field sensor 12 for detecting an induced magnetic field generated by an internal coil 10a mounted in a capsule medical device 10, and guiding magnetic field generating coils (opposing coils) 313A and 313B for generating a guiding magnetic field.

In addition, the position detecting magnetic field generating coil driving unit 15 and the position detection control unit 16 are provided for the position detecting magnetic field generating coil 11 and the magnetic field sensor 12, respectively.

A guiding magnetic field generating coil driving unit 317, the guiding control unit 18, and a capacitor (element) 319 are provided for the guiding magnetic field generating coils 313A and 313B.

Note that, in the medical-device magnetic guiding and position detecting system 301 according to the present embodiment, the frequency of the position detecting magnetic field is higher than that of the guiding magnetic field.

As shown in FIG. 11, each of the guiding magnetic field generating coils 313A and 313B is composed of a substantially flat coil. The guiding magnetic field generating coils 313A and 313B are connected in series. In addition, the guiding magnetic field generating coils 313A and 313B are electrically connected to a guiding magnetic field generating coil driving unit 317. For example, an L terminal (Live terminal) of the guiding magnetic field generating coil driving unit 317 is connected to the guiding magnetic field generating coil 313A whereas an N terminal (Neutral terminal) of the guiding magnetic field generating coil driving unit 317 is connected to the guiding magnetic field generating coil 313B.

The guiding magnetic field generating coil driving unit 317 is electrically connected to the guiding control unit 18 so as to receive a control signal generated by the guiding control unit 18.

The guiding magnetic field generating coil 313A is disposed in the vicinity of the position detecting magnetic field generating coil 11 so as to face the position detecting magnetic field generating coil 11. In addition, the guiding magnetic field generating coil 313A is disposed on the opposite side of the position detecting magnetic field generating coil 11 from the capsule medical device 10. The guiding magnetic field generating coil 313B is disposed in the vicinity of the magnetic field sensor 12 so as to face the magnetic field sensor 12. In addition, the guiding magnetic field generating coil 313B is disposed on the opposite side of the magnetic field sensor 12 from the capsule medical device 10.

One terminal of the capacitor 319 is connected to a point between the guiding magnetic field generating coils 313A and 313B. The other terminal of the capacitor 319 is connected to a point between the guiding magnetic field generating coil 313B and the guiding magnetic field generating coil driving unit 317.

The capacitor 319 has an impedance lower than that of the guiding magnetic field generating coil 313A or 313B at least at the frequency of the position detecting magnetic field. In addition, at the frequency of the guiding magnetic field, the capacitor 319 has an impedance higher than that of the guiding magnetic field generating coil 313A or 313B.

The relationship between an impedance $Z_L$ of the guiding magnetic field generating coil 313A or 313B and an impedance $Z_C$ of the capacitor 319 is described next.

The assumption used for determining the relationship between the impedance $Z_L$ and the impedance $Z_C$ is described first.

Let $S_0$ denote a voltage level in accordance with the strength of the position detecting magnetic field detected by the magnetic field sensor 12. This level $S_0$ is used as a reference level of the medical-device magnetic guiding and position detecting system 301.

Let $SNR_0$ denote the S/N ratio (signal-to-noise ratio) that the position detecting system 301 currently has as the performance thereof. In contrast, let $SNR_1$ denote the S/N ratio required for detecting the position of the capsule medical device 10 with sufficient accuracy. When evaluating an event that can change the signal strength, the values of noise in the both states can be considered to be the same. This value is referred to as $N_0$. Note that each of the two SNRs is greater than or equal to 1.

In the case where the capacitor 319 is not present, when a mutual induction magnetic field that is a reversed-phase magnetic field is generated in the guiding magnetic field generating coil 313B, the position detecting magnetic field and the mutual induction magnetic field cancel each other out at the position of the magnetic field sensor 12. Thus, the level of the position detecting magnetic field detected by the magnetic field sensor 12 may be reduced to the level $N_0$. That is, the conditions, such as the numbers of windings of the coils, the positions of the coils, and the radius of the coils, of the position detecting magnetic field generating coil 11 and the guiding magnetic field generating coils 313A and 313B, are set so that the level of the position detecting magnetic field detected by the magnetic field sensor 12 is reduced to the level $N_0$.

In addition, it is assumed that the level of the induction magnetic field formed by the internal coil 10a and detected by the magnetic field sensor 12 is equal to the reference level (i.e., the level $S_0$). That is, it is assumed that the conditions of the internal coil 10a, such as the performance and the position of the internal coil 10a, is determined so that the level of the induction magnetic field detected by the magnetic field sensor 12 is equal to the level $S_0$.

Note that the above-described assumption is determined in order to obtain a rough indication of the value of the impedance of the capacitor 319. In general, the level of the induction magnetic field detected by the magnetic field sensor 12 is less than the level $S_0$.

In addition, in terms of the mutual induction magnetic field which is a reversed-phase magnetic field emanating from the guiding magnetic field generating coil 313B, let α denote an attenuation ratio of the mutual induction magnetic field before and after the capacitor 319 is provided. That is, α denotes a ratio of the strength of the mutual induction magnetic field before the capacitor 319 is provided to the strength of the mutual induction magnetic field attenuated by the provision of the capacitor 319.

On the basis of the above-described assumptions, if the capacitor 319 is provided between the guiding magnetic field generating coils 313A and 313B, the level (signal strength) of the induction magnetic field formed by the internal coil 10a and detected by the magnetic field sensor 12 is $S_0(1-\alpha)$. The relationship between the impedance $Z_L$ and the impedance $Z_C$ that satisfies the required S/N ratio ($SNR_1$) at that signal strength is obtained next.

Here, the above-described relationship is expressed as follows:

$$S_0(1-\alpha)=SNR_1 \times N_0 \quad (1)$$

Here, since $S_0/N_0=SNR_0$, equation (1) is rewritten to obtain α as follows:

$$\alpha=1-(SNR_1)/(SNR_0) \quad (2)$$

In equation (2), if the device S/N ratio ($SNR_0$) is 100000 and the required S/N ratio ($SNR_1$) is 99900, α is 0.001. That is, equation (2) indicates that allowance of the device S/N ratio with respect to the required S/N ratio changes the relationship between the impedance $Z_L$ and the impedance $Z_C$.

In addition, as noted above, α represents the attenuation ratio of the reversed-phase magnetic field emanating from the guiding magnetic field generating coil 313B. The strength of the reversed-phase magnetic field is proportional to an electrical current flowing in the guiding magnetic field generating coil 313B. That is, by computing the attenuation ratio of the electrical current flowing in the guiding magnetic field generating coil 313B, the attenuation ratio of the strength of the reversed-phase magnetic field can be obtained.

Figure 14:
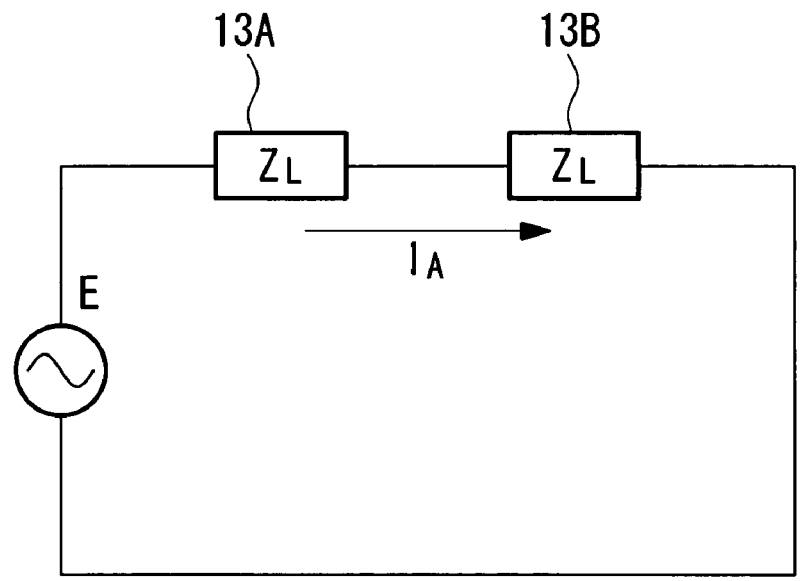
FIG. 14 is a diagram illustrating the configuration of a circuit formed by guiding magnetic field generating coils and the position detecting magnetic field generating coil.

FIG. 14 is a diagram illustrating a circuit formed by the guiding magnetic field generating coils 313A and 313B and the position detecting magnetic field generating coil 11.

Here, the relationship among an electromotive force, an impedance, and an electrical current of the circuit formed by the guiding magnetic field generating coils 313A and 313B and the position detecting magnetic field generating coil 11 is given by the following equation:

$$I_A=E/(2Z_L) \quad (3)$$

where $Z_L$ is the impedance at a frequency of the position detecting magnetic field generated by the guiding magnetic field generating coils 313A and 313B, E is the electromotive force induced in the guiding magnetic field generating coil 313A by the position detecting magnetic field, and $I_A$ is an electrical current flowing in the circuit shown in FIG. 14.

Figure 15:
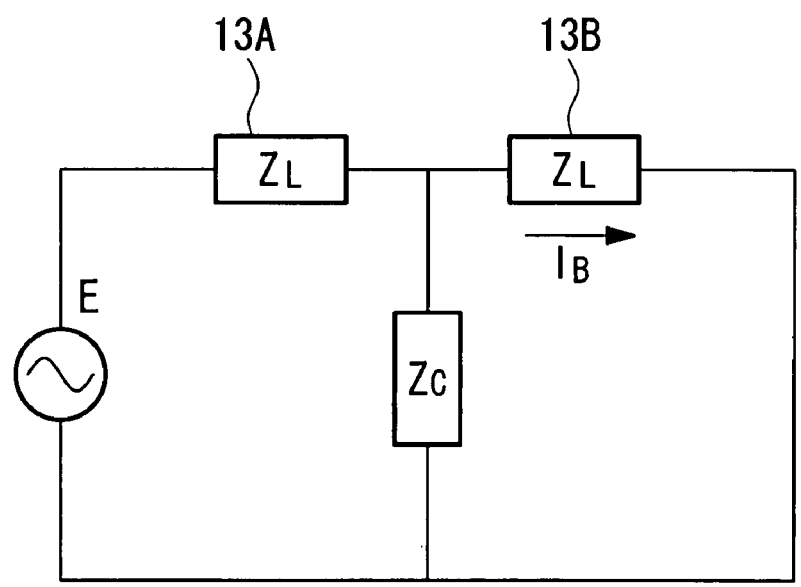
FIG. 15 illustrates the configuration of a circuit formed by guiding magnetic field generating coils, a capacitor, and a position detecting magnetic field generating coil.

FIG. 15 illustrates the configuration of a circuit formed by the guiding magnetic field generating coils 313A and 313B, the capacitor 319, and the position detecting magnetic field generating coil 11.

Here, the relationship among an electromotive force, an impedance, and an electrical current of the circuit formed by the guiding magnetic field generating coils 313A and 313B, the capacitor 319, and the position detecting magnetic field generating coil 11 is given by the following equation:

$$I_B=\{Z_C/(Z_L+Z_C)\}/\{E/(Z_L+Z_L//Z_C)\} \quad (4)$$

where $Z_C$ is the impedance of the capacitor 319 at a frequency of the position detecting magnetic field, $I_B$ is an electrical current flowing in the circuit shown in FIG. 15, and "//" represents an operation to compute the impedance of parallel elements.

According to the above-described assumptions, the attenuation ratio can be computed using the following equation:

$$\alpha=I_B/I_A \quad (5)$$

By substituting equations (3) and (4) into equation (5), the following equation is obtained:

$$\alpha=1/(1+Z_L/2Z_C) \quad (6)$$

$Z_C/Z_L$ can be obtained using equations (2) and (6) as follows:

$$Z_C/Z_L=1/(2\times\{SNR_0/(SNR_0-SNR_1)-1\}) \quad (7)$$

Accordingly, if the relationship between the impedance $Z_L$ and the impedance $Z_C$ satisfies equation (7), the medical-device magnetic guiding and position detecting system 301 according to the present embodiment can prevent formation of an area where the combined magnetic field composed of the position detecting magnetic field and the mutual induction magnetic field emanating from the guiding magnetic field generating coil is substantially zero. Accordingly, a decrease in the strength of the position detecting magnetic field in the operating range of the capsule medical device 10 can be prevented. In addition, the guiding magnetic field can be generated by the guiding magnetic field generating coils 313A and 313B at least at the frequency of the guiding magnetic field.

Figure 12:
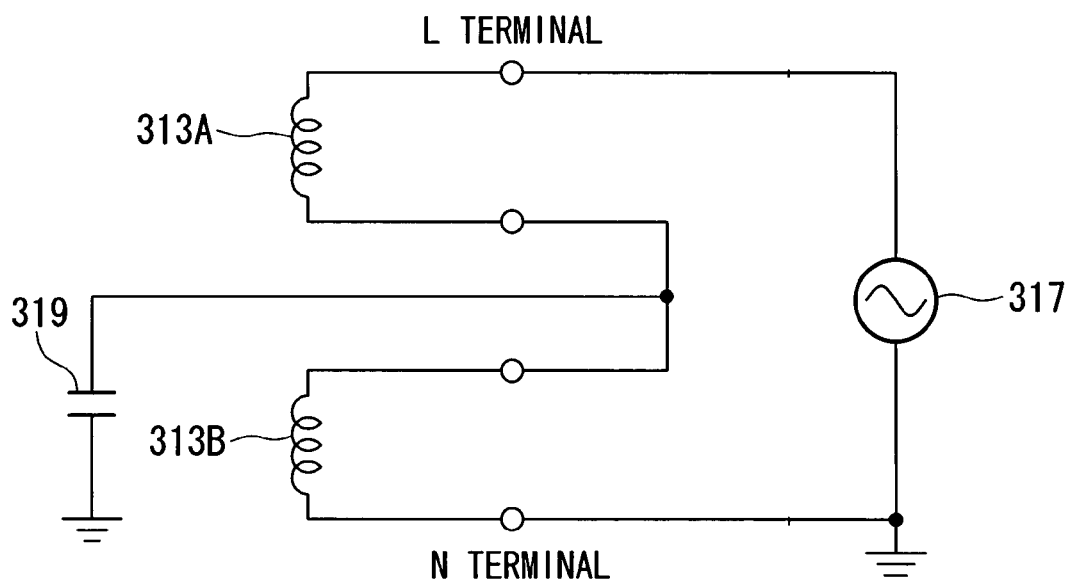
FIG. 12 illustrates the configuration of a circuit formed by the guiding magnetic field generating coils shown in FIG. 11.

FIG. 12 illustrates the configuration of a circuit formed by the guiding magnetic field generating coils shown in FIG. 11.

As shown in FIG. 12, the guiding magnetic field generating coils 313A and 313B are connected in series. The L terminal of the guiding magnetic field generating coil driving unit 317 is connected to the guiding magnetic field generating coil 313A whereas the N terminal of the guiding magnetic field generating coil driving unit 317 is connected to the guiding magnetic field generating coil 313B. Additionally, the N terminal of the guiding magnetic field generating coil driving unit 317 is connected to ground. One terminal of the capacitor 319 is connected to a point between the guiding magnetic field generating coils 313A and 313B. The other terminal of the capacitor 319 is connected to a point between the guiding magnetic field generating coil 313B and the N terminal of the guiding magnetic field generating coil driving unit 317. Therefore, the other terminal of the capacitor 319 can be considered to be connected to ground.

The operation of the medical-device magnetic guiding and position detecting system 301 having such a configuration is described next.

The operation of the medical-device magnetic guiding and position detecting system 301 for detecting the position of the capsule medical device 10, such as formation of a position detecting magnetic field by the position detecting magnetic field generating coil 11 and the formation of an induction magnetic field by the internal coil 10a, is similar to that of the first embodiment, and therefore, description thereof is not repeated here.

The operation of the guiding magnetic field generating coils 313A and 313B, which is the feature of the present embodiment, is described next.

The formation of the guiding magnetic field by the guiding magnetic field generating coils 313A and 313B is described first.

As shown in FIG. 11, the guiding control unit 18 generates a guiding control signal which is an alternating current signal having a predetermined frequency. The guiding control signal is output to the guiding magnetic field generating coil driving unit 317.

The guiding magnetic field generating coil driving unit 317 amplifies the input guiding control signal to a predetermined strength so as to generate a driving electrical current for driving the guiding magnetic field generating coils 313A and 313B. The driving electrical current is output from the L terminal to the guiding magnetic field generating coils 313A and 313B that are connected in series. Upon receiving the driving electrical current, the guiding magnetic field generating coils 313A and 313B form guiding magnetic fields therearound.

The frequency of the driving electrical current for causing the guiding magnetic field generating coils 313A and 313B to form guiding magnetic fields is the same as the frequency of the guiding magnetic fields. At the frequency of the driving electrical current, the impedance of the capacitor 319 is higher than that of the guiding magnetic field generating coil 313A or 313B. Therefore, the driving electrical current flows from the guiding magnetic field generating coil 313A to the guiding magnetic field generating coil 313B. Consequently, the guiding magnetic field generating coils 313A and 313B can generate the guiding magnetic fields.

The case where the position detecting magnetic field formed by the position detecting magnetic field generating coil 11 acts on the guiding magnetic field generating coil 313A is described next.

Figure 13:
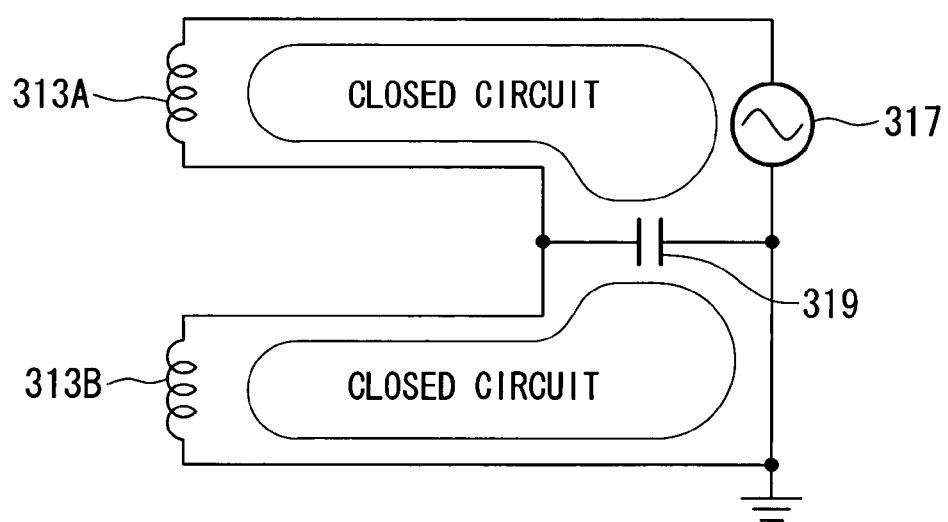
FIG. 13 illustrates a flow of an electrical current having a frequency that is the same as the frequency of a position detecting magnetic field in the circuit of the guiding magnetic field generating coils shown in FIG. 12.

FIG. 13 illustrates a flow of an electrical current having a frequency that is the same as the frequency of the position detecting magnetic field in the circuit of the guiding magnetic field generating coils shown in FIG. 12.

The guiding magnetic field generating coil 313A is connected to the guiding magnetic field generating coil driving unit 317 having a significantly low impedance. Accordingly, when the position detecting magnetic field passes through the guiding magnetic field generating coil 313A, an electrical current flows via the coil 313B due to an electromotive force induced at either end of the guiding magnetic field generating coil 313A. This induced electrical current that is generated by the electromotive force and that flows in the circuit has the same frequency as that of the position detecting magnetic field.

When the induced electrical current having the same frequency as that of the position detecting magnetic field flows in the circuit formed by the guiding magnetic field generating coils 313A and 313B, the guiding magnetic field generating coil driving unit 317, and the capacitor 319, the above-described circuit functions as a circuit including two closed circuits, as shown in FIG. 13. One of the two closed circuits includes the guiding magnetic field generating coil 313A, the capacitor 319, and the guiding magnetic field generating coil driving unit 317. The other closed circuit includes the guiding magnetic field generating coil 313B and the capacitor 319.

That is, at a frequency that is the same as that of the position detecting magnetic field, the capacitor 319 has an impedance lower than those of the guiding magnetic field generating coil 313A or 313B. Accordingly, the induced electrical current flows from the guiding magnetic field generating coil 313A to the capacitor 319. Therefore, the induced electrical current does not flow in the guiding magnetic field generating coil 313B. As a result, a magnetic field in a direction that cancels out the position detecting magnetic field is not generated in the guiding magnetic field generating coil 313B.

In the above-described configuration, one end of the capacitor 319 is connected to the point between the guiding magnetic field generating coils 313A and 313B. The other end of the capacitor 319 is connected to ground at the point between the guiding magnetic field generating coil 313B and the N terminal of the guiding magnetic field generating coil driving unit 317. Accordingly, even when the condition under which mutual induction due to the position detecting magnetic field is induced in the guiding magnetic field generating coil 313A occurs, an electrical current generated by the electromotive force due to the mutual induction does not flow from the guiding magnetic field generating coil 313A to the guiding magnetic field generating coil 313B. As a result, the occurrence of a magnetic field having a phase that is the same as that of the mutual induction magnetic field having a reversed phase to that of the position detecting magnetic field can be prevented.

That is, an area where the strength of the combined magnetic field composed of the position detecting magnetic field and the mutual induction magnetic field emanating from the guiding magnetic field generating coil is substantially zero is not formed. As a result, a decrease in the strength of the position detecting magnetic field in an operating area of the capsule medical device 10 can be prevented.

However, since the capacitor 319 has an impedance higher than that of the guiding magnetic field generating coil 313A or 313B at least at the frequency of the guiding magnetic field, an electrical current that causes the guiding magnetic field generating coils 313A and 313B to generate a driving magnetic field does not flow in the capacitor 319. Consequently, the guiding magnetic field can be generated by the guiding magnetic field generating coils 313A and 313B.

As noted above, the guiding magnetic field generating coil driving unit 317 may include the L terminal and the N terminal. Only the L terminal may be used for the output. Alternatively, the guiding magnetic field generating coil driving unit 317 may include two L terminals. The guiding magnetic field generating coil driving unit 317 may drive the guiding magnetic field generating coils 313A and 313B using the difference between the outputs of the two L terminals (i.e., a differential output).

In such a case, it is desirable that the terminal of the capacitor 319 that is connected to the point between the guiding magnetic field generating coil 313B and the N terminal of the guiding magnetic field generating coil driving unit 317 is connected to the ground potential of the guiding magnetic field generating coil driving unit 317.

Fifth Embodiment

A fifth embodiment of the present invention is described next with reference to FIGS. 16 to 18.

The basic configuration of the medical-device magnetic guiding and position detecting system according to the present embodiment is similar to that of the first embodiment except for the structure of a guiding magnetic field generating coil driving unit. Therefore, according to the present embodiment, only the structure and related components of the guiding magnetic field generating coil driving unit are described next with reference to FIGS. 16 to 18. Descriptions of the other components are not repeated.

Figure 16:
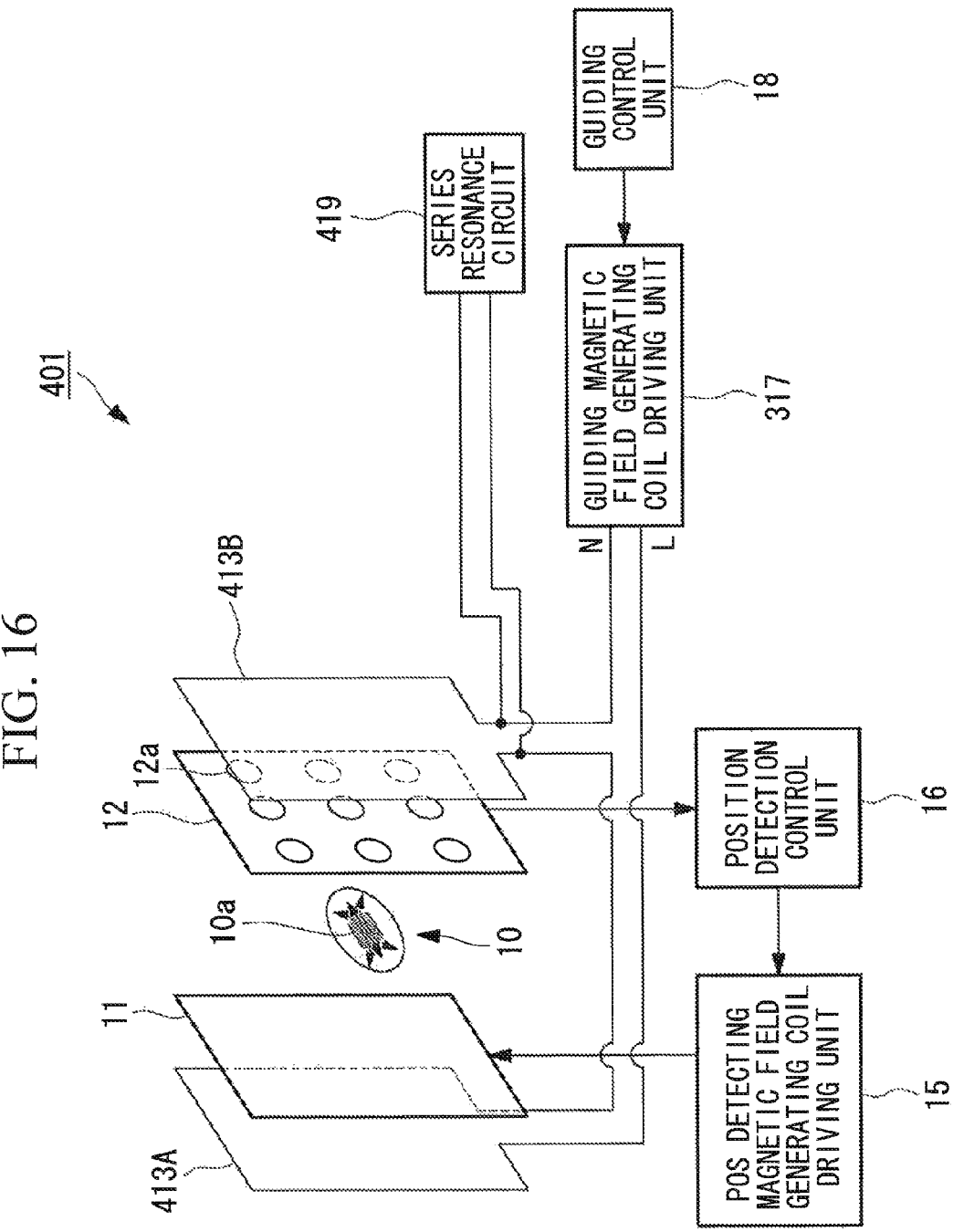
FIG. 16 is a block diagram of the schematic configuration of a medical-device magnetic guiding and position detecting system according to a fifth embodiment of the present invention.

FIG. 16 is a block diagram of the medical-device magnetic guiding and position detecting system according to the present embodiment.

In FIG. 16, the same components as those illustrated and described in relation to the first embodiment are designated by the same reference numerals. Descriptions of these components are not repeated here.

As shown in FIG. 16, a medical-device magnetic guiding and position detecting system 401 includes a position detecting magnetic field generating coil 11 for generating a position detecting magnetic field, a magnetic field sensor 12 for detecting an induced magnetic field generated by an internal coil 10a mounted in a capsule medical device 10, and guiding magnetic field generating coils (opposing coils) 413A and 413B for generating a guiding magnetic field.

In addition, the position detecting magnetic field generating coil driving unit 15 for driving the position detecting magnetic field generating coil and the position detection control unit 16 are provided for the position detecting magnetic field generating coil 11 and the magnetic field sensor 12, respectively.

A guiding magnetic field generating coil driving unit 317, the guiding control unit 18, and a series resonance circuit (element) 419 are provided for the guiding magnetic field generating coils 413A and 413B.

As shown in FIG. 16, each of the guiding magnetic field generating coils 413A and 413B is composed of a substantially flat coil. The guiding magnetic field generating coils 413A and 413B are connected in series. In addition, the guiding magnetic field generating coils 413A and 413B are electrically connected to a guiding magnetic field generating coil driving unit 317. For example, an L terminal of the guiding magnetic field generating coil driving unit 317 is connected to the guiding magnetic field generating coil 413A whereas an N terminal of the guiding magnetic field generating coil driving unit 317 is connected to the guiding magnetic field generating coil 413B.

The guiding magnetic field generating coil driving unit 317 is electrically connected to the guiding control unit 18 so as to receive a control signal generated by the guiding control unit 18.

The guiding magnetic field generating coil 413A is disposed in the vicinity of the position detecting magnetic field generating coil 11 so as to face the position detecting magnetic field generating coil 11. In addition, the guiding magnetic field generating coil 413A is disposed on the opposite side of the position detecting magnetic field generating coil 11 from the capsule medical device 10. The guiding magnetic field generating coil 413B is disposed in the vicinity of the magnetic field sensor 12 so as to face the magnetic field sensor 12. In addition, the guiding magnetic field generating coil 413B is disposed on the opposite side of the magnetic field sensor 12 from the capsule medical device 10.

Figure 17:
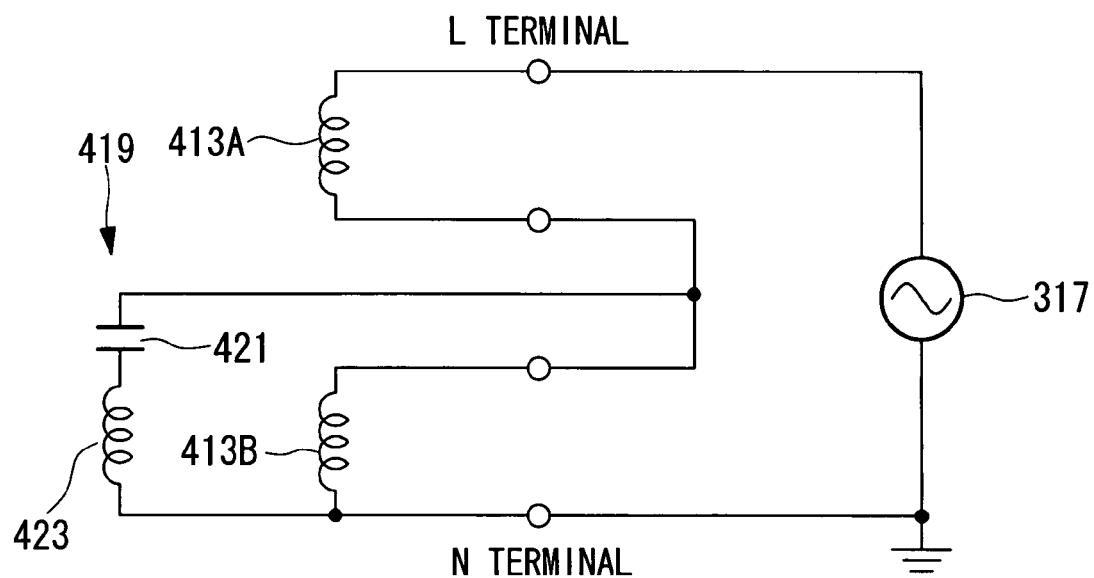
FIG. 17 illustrates the configuration of a circuit formed by guiding magnetic field generating coils shown in FIG. 16.

FIG. 17 is a circuit diagram of the guiding magnetic field generating coils shown in FIG. 16.

As shown in FIG. 17, a coil 421 is connected to a capacitor 423 in series to form the series resonance circuit 419. As shown in FIG. 17, one terminal of the series resonance circuit 419 is connected to a point between the guiding magnetic field generating coils 413A and 413B. The other terminal of the series resonance circuit 419 is connected to a point between the guiding magnetic field generating coil 413B and the guiding magnetic field generating coil driving unit 317.

The series resonance circuit 419 produces series resonance at least at the frequency of the position detecting magnetic field. That is, let L [H] denote the inductance of the coil 421 and C [F] denote the capacitance of the capacitor 423. Then, the series resonance frequency of the series resonance circuit 419 is $1/\{2\pi(LC)^{1/2}\}$ [Hz]. The inductance L of the coil 421 and the capacitance C of the capacitor 423 are determined so that this series resonance frequency is equal to the frequency of the position detecting magnetic field.

The operation of the medical-device magnetic guiding and position detecting system 401 having such a configuration is described next.

The operation of the medical-device magnetic guiding and position detecting system 401 for detecting the position of the capsule medical device 10, such as formation of a position detecting magnetic field by the position detecting magnetic field generating coil 11 and the formation of an induction magnetic field by the internal coil 10a, is similar to that of the first embodiment, and therefore, description thereof is not repeated here.

The operation of the guiding magnetic field generating coils 413A and 413B, which is the feature of the present embodiment, is described next.

The formation of the guiding magnetic field by the guiding magnetic field generating coils 413A and 413B is described first.

As shown in FIG. 16, the guiding control unit 18 generates a guiding control signal which is an alternating current signal having a predetermined frequency. The guiding control signal is output to the guiding magnetic field generating coil driving unit 317.

The guiding magnetic field generating coil driving unit 317 amplifies the input guiding control signal to a predetermined strength so as to generate a driving electrical current for driving the guiding magnetic field generating coils 413A and 413B. The driving electrical current is output from the L terminal to the guiding magnetic field generating coils 413A and 413B that are connected in series. Upon receiving the driving electrical current, the guiding magnetic field generating coils 413A and 413B form guiding magnetic fields therearound.

The frequency of the driving electrical current for causing the guiding magnetic field generating coils 413A and 413B to form guiding magnetic fields is the same as the frequency of the guiding magnetic fields. Since the series resonance circuit 419 does not produce series resonance at the frequency of the driving electrical current, the driving electrical current flows from the guiding magnetic field generating coil 413A to the guiding magnetic field generating coil 413B. Consequently, the guiding magnetic field generating coils 413A and 413B can generate the guiding magnetic fields.

The case where the position detecting magnetic field formed by the position detecting magnetic field generating coil 11 acts on the guiding magnetic field generating coil 413A is described next.

Figure 18:
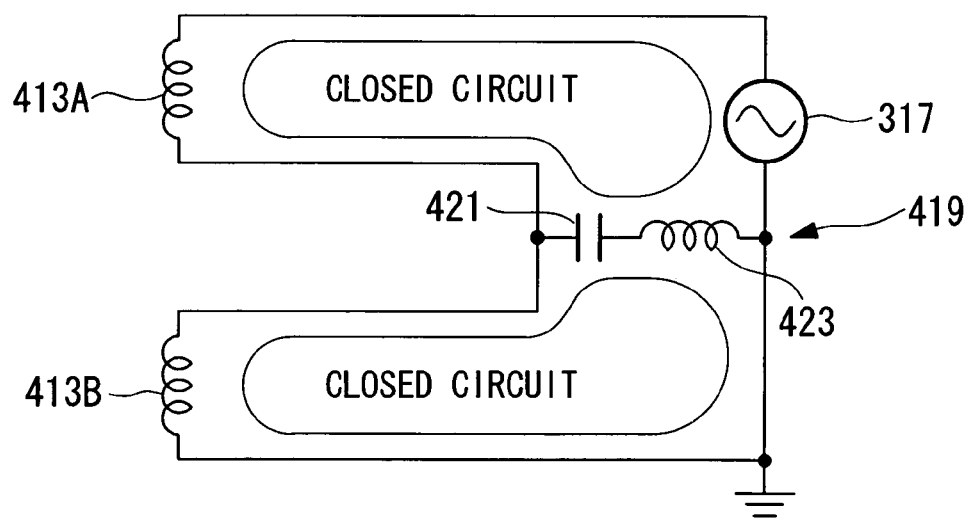
FIG. 18 illustrates a flow of an electrical current having a frequency that is the same as the frequency of a position detecting magnetic field in the circuit of the guiding magnetic field generating coils shown in FIG. 16.

FIG. 18 is a circuit diagram illustrating a flow of an electrical current having the frequency that is the same as the frequency of the position detecting magnetic field in the circuit formed by the guiding magnetic field generating coils shown in FIG. 16.

Since the guiding magnetic field generating coil 413A is connected to the guiding magnetic field generating coil driving unit 317 having a significantly low impedance, electromotive forces are induced at either end of the guiding magnetic field generating coil 413A when the position detecting magnetic field passes through the guiding magnetic field generating coil 413A. This induced electrical current that is generated by the electromotive force and that flows in the circuit has the same frequency as that of the position detecting magnetic field.

When the induced electrical current having the same frequency as that of the position detecting magnetic field flows in the circuit formed by the guiding magnetic field generating coils 413A and 413B, the guiding magnetic field generating coil driving unit 317, and the series resonance circuit 419, the above-described circuit functions as a circuit including two closed circuits, as shown in FIG. 18. One of the two closed circuits includes the guiding magnetic field generating coil 413A, the series resonance circuit 419, and the guiding magnetic field generating coil driving unit 317. The other closed circuit includes the guiding magnetic field generating coil 413B and the series resonance circuit 419.

That is, since the series resonance circuit 419 produces series resonance at a frequency that is the same as the frequency of the position detecting magnetic field, the induced electrical current flows from the guiding magnetic field generating coil 413A to the series resonance circuit 419. Therefore, the induced electrical current does not flow in the guiding magnetic field generating coil 413B. As a result, a magnetic field in a direction that cancels out the position detecting magnetic field is not generated in the guiding magnetic field generating coil 413B.

The above-described configuration includes the series resonance circuit 419 having a series resonance frequency that is substantially the same as the frequency of the position detecting magnetic field. Accordingly, even when the condition that induces mutual induction due to the position detecting magnetic field in the guiding magnetic field generating coil 413A occurs, an electrical current generated by the electromotive force due to the mutual induction does not flow from the guiding magnetic field generating coil 413A to the guiding magnetic field generating coil 413B.

That is, since a closed circuit is formed by the guiding magnetic field generating coil 413A, the series resonance circuit 419, and the guiding magnetic field generating coil driving unit 317 at the frequency of the position detecting magnetic field, the electrical current due to the mutual induction does not flow in the guiding magnetic field generating coil 413B.

In contrast, at a frequency other than the frequency of the position detecting magnetic field, for example, at the frequency of the guiding magnetic field, the impedance of the series resonance circuit 419 is higher than that of the guiding magnetic field generating coil 413B. Accordingly, an electrical current that generates a guiding magnetic field flows in the guiding magnetic field generating coil 413B. Consequently, the guiding magnetic field generating coils 413A and 413B can generate a guiding magnetic field.

Sixth Embodiment

A sixth embodiment of the present invention is described next with reference to FIGS. 19 and 20.

The basic configuration of the medical-device magnetic guiding and position detecting system according to the present embodiment is similar to that of the first embodiment except for the structure of a guiding magnetic field generating coil driving unit. Therefore, according to the present embodiment, only the structure and related components of the guiding magnetic field generating coil driving unit are described next with reference to FIGS. 19 and 20. Descriptions of the other components are not repeated.

Figure 19:
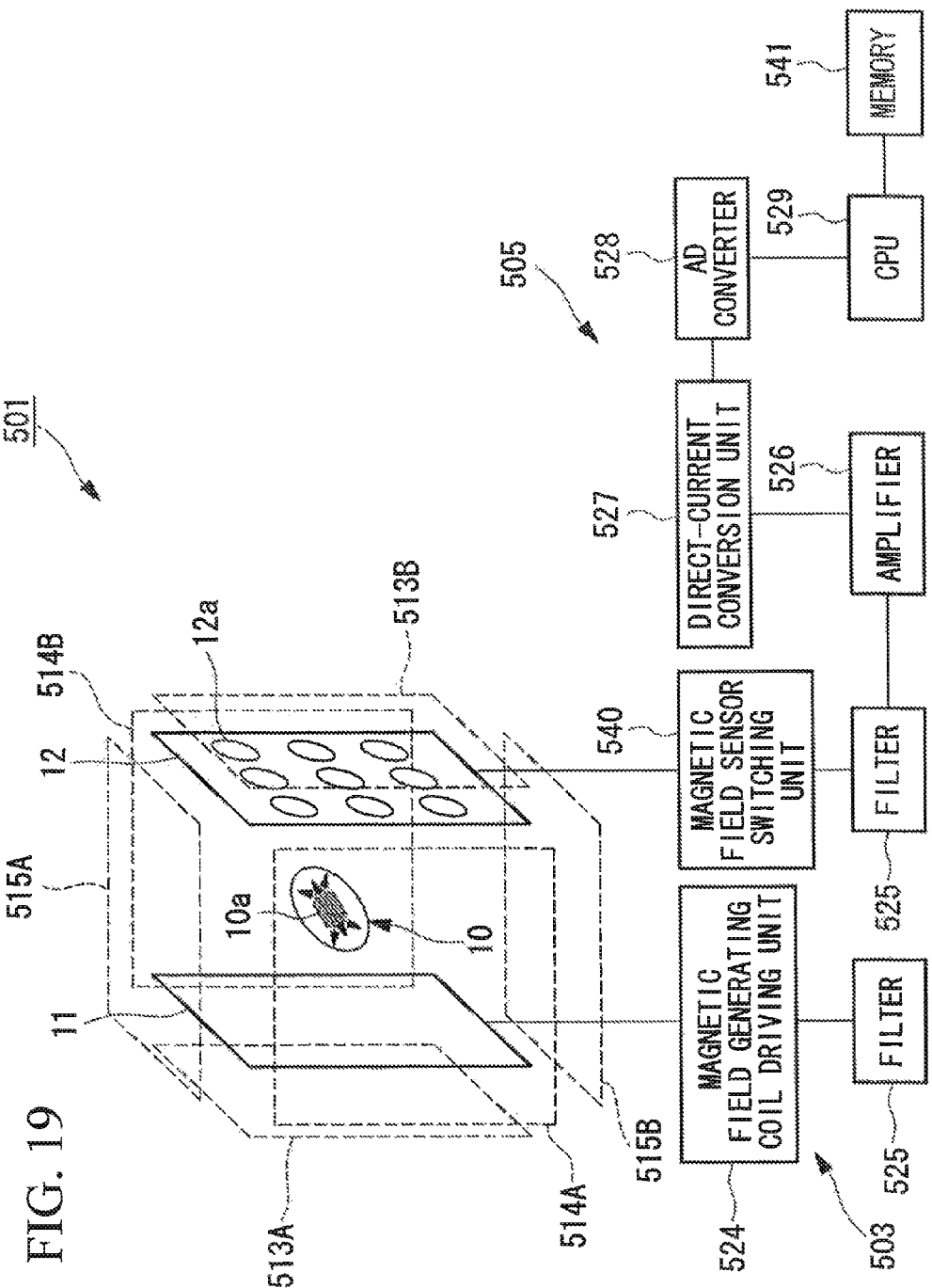
FIG. 19 is a block diagram of the schematic configuration of a medical-device magnetic guiding and position detecting system according to a sixth embodiment of the present invention.

FIG. 19 is a block diagram of the medical-device magnetic guiding and position detecting system according to the present embodiment.

In FIG. 19, the same components as those illustrated and described in relation to the first embodiment are designated by the same reference numerals. Descriptions of these components are not repeated here.

As shown in FIG. 19, a medical-device magnetic guiding and position detecting system 501 includes a position detecting magnetic field generating coil 11 for generating a position detecting magnetic field, a magnetic field sensor 12 for detecting an induced magnetic field generated by an internal coil 10a mounted in a capsule medical device 10, and guiding magnetic field generating coils (opposing coils) 513A, 513B, 514A, 514B, 515A, and 515B for generating a guiding magnetic field for guiding the capsule medical device to a predetermined position in a body cavity.

A driving unit 503 for driving and controlling the position detecting magnetic field generating coil 11 is provided for the position detecting magnetic field generating coil 11. A detection unit 505 for processing a signal output from the magnetic field sensor 12 is provided for the magnetic field sensor 12.

The driving unit 503 includes a signal generating unit 523 and a magnetic field generating coil driving unit 524. The signal generating unit 523 outputs an alternating current signal having the frequency of an alternating magnetic field generated by the position detecting magnetic field generating coil 11. The magnetic field generating coil driving unit 524 amplifies the alternating current signal input from the signal generating unit 523 so as to drive the position detecting magnetic field generating coil 11.

The detection unit 505 includes a filter 525 for cutting unnecessary frequency components included in the signal output from the detection coils 12a, an amplifier 526 for amplifying the output signal without the unnecessary frequency components, a direct-current conversion unit 527 for converting the amplified output signal from an alternating current to a direct current, and an AD converter 528 for converting the direct current from an analog signal to a digital signal, a CPU 529 for performing computation on the basis of the digital output signal, and a magnetic field sensor switching unit 530 for selecting a signal output from a predetermined magnetic field sensor 12 from among the output signals output from all the magnetic field sensors 12.

A memory 531 is connected to the CPU 529. The memory 531 stores the output signal acquired when the capsule medical device 10 is not disposed. By providing the memory 531, an operation for subtracting the output signal acquired when the capsule medical device 10 is not disposed from the output signal acquired when the capsule medical device 10 is disposed can be easily performed. Thus, only the output signal related to the induction magnetic field emanating from the internal coil 10a of the capsule medical device 10 can be easily detected.

In addition, the direct-current conversion unit 527 may be, but is not limited to, an RMS converter. Alternatively, a known AC-DC converter may be employed.

The guiding magnetic field generating coils 513A and 513B, the guiding magnetic field generating coils 514A and 514B, and the guiding magnetic field generating coils 515A and 515B are disposed so as to face each other with a distance satisfying the Helmholtz condition or a condition near the Helmholtz condition therebetween. Therefore, the spatial intensity gradient of the magnetic fields generated by the guiding magnetic field generating coils 513A and 513B, the guiding magnetic field generating coils 514A and 514B, and the guiding magnetic field generating coils 515A and 515B is reduced to zero or reduced to a small value that is negligible.

In addition, the guiding magnetic field generating coils 513A and 513B, the guiding magnetic field generating coils 514A and 514B, and the guiding magnetic field generating coils 515A and 515B are disposed so that the center axis line of the guiding magnetic field generating coils 513A and 513B, the center axis line of the guiding magnetic field generating coils 514A and 514B, and the center axis line of the guiding magnetic field generating coils 515A and 515B are perpendicular to each other. Thus, a rectangle parallelepiped space is formed by the guiding magnetic field generating coils 513A and 513B, the guiding magnetic field generating coils 514A and 514B, and the guiding magnetic field generating coils 515A and 515B. As shown in FIG. 19, the rectangle parallelepiped space serves as an operating space of the capsule medical device 10.

FIG. 20 is a block diagram illustrating the structure of the guiding magnetic field generating coils shown in FIG. 19.

The guiding magnetic field generating coils 514A and 514B are electrically connected in series. Additionally, the guiding magnetic field generating coils 515A and 515B are electrically connected in series. However, since the guiding magnetic field generating coils 513A and 513B are connected to different guiding magnetic field generating coil driving units, the guiding magnetic field generating coils 513A and 513B, unlike the other coils, are not electrically connected in series. More specifically, guiding magnetic field generating coil driving units 513C-1 and 513C-2 are connected to the guiding magnetic field generating coils 513A and 513B so that the outputs from the guiding magnetic field generating coil driving units 513C-1 and 513C-2 are input to the guiding magnetic field generating coils 513A and 513B, respectively. Furthermore, the guiding magnetic field generating coils 514A and 514B are electrically connected to a guiding magnetic field generating coil driving unit 514C in series whereas the guiding magnetic field generating coils 515A and 515B are electrically connected to a guiding magnetic field generating coil driving unit 515C in series. A signal generator 513D is electrically connected to the guiding magnetic field generating coil driving units 513C-1 and 513C-2 so that the same signal is input from the signal generator 513D to the guiding magnetic field generating coil driving units 513C-1 and 513C-2. In addition, signal generators 514D and 515D are electrically connected to the guiding magnetic field generating coil driving units 514C and 515C so that signals are input from the signal generators 514D and 515D to the guiding magnetic field generating coil driving units 514C and 515C, respectively. A guiding control unit 516 is electrically connected to the signal generators 513D, 514D, and 515D so that a control signal is input from the guiding control unit 516 to the signal generators 513D, 514D, and 515D. An input unit 517 is electrically connected to the guiding control unit 516 so that a signal is input from the input unit 517 to the guiding control unit 516. The input unit 517 is used for externally inputting an instruction for determining the guiding direction of the capsule medical device 10.

The operation of the medical-device magnetic guiding and position detecting system 501 having such a configuration is described next.

The operation performed by the medical-device magnetic guiding and position detecting system 501 for detecting the position of the capsule medical device 10 is described first.

As shown in FIG. 19, in the driving unit 503, the signal generating unit 523 generates an alternating current signal having a predetermined frequency and outputs the alternating current signal to the magnetic field generating coil driving unit 524. The magnetic field generating coil driving unit 524 amplifies the input alternating current signal to a predetermined strength and outputs the amplified alternating current signal to the position detecting magnetic field generating coil 11. Upon receiving the amplified alternating current signal, the position detecting magnetic field generating coil 11 generates an alternating magnetic field therearound.

When the above-described alternating magnetic field passes through the capsule medical device 10, a resonant electrical current having a predetermined frequency is induced in a subject closed circuit mounted in the capsule medical device 10 and including the internal coil 10a. When the resonant electrical current is induced in the closed circuit of the capsule medical device 10, the internal coil 10a forms an induction magnetic field having a predetermined frequency caused by the resonant electrical current.

Since the magnetic fluxes of the above-described alternating magnetic field and induction magnetic field pass through the magnetic field sensor 12, the magnetic field sensor 12 captures the magnetic flux that is a sum of the magnetic fluxes of the above-described alternating magnetic field and induction magnetic field and generates an output signal that is an induced electrical current based on the change in the passing magnetic fluxes. The output signal of the magnetic field sensor 12 is output to the detection unit 505.

In the detection unit 505, the output signal input to the detection unit 505 is delivered to the magnetic field sensor switching unit 530 first. The magnetic field sensor switching unit 530 passes only the output signal used for detecting the position of the capsule medical device 10 therethrough and blocks the other output signals.

For example, to select the output signal, the magnetic field sensor switching unit 530 may select the output signal having a strong signal strength or the output signal delivered from the magnetic field sensor 12 located close to the capsule medical device 10.

In addition, as noted above, the magnetic field sensor switching unit 530 may be disposed between the magnetic field sensor 12 and the filter 525 so that only the output signal used for position detection is selected. Alternatively, the magnetic field sensor switching unit 530 may switch the connections between the magnetic field sensor switching unit 530 and the plurality of magnetic field sensors 12 so that the signals output from all the magnetic field sensors 12 are input to the detection unit 505 in a time-multiplexing manner. Alternatively, by connecting a system including the filter 525 to the AD converter 528 with each of the magnetic field sensors 12, the need for the magnetic field sensor switching unit 530 can be eliminated. Thus, the selection of one of the output signals is not needed. That is, a variety of method can be applied.

The selected output signal is input to the filter 525. The filter 525 removes a frequency component in the output signal that is not used for the position detection. For example, the filter 525 removes a low-frequency component in the output signal. The output signal that does not include unnecessary components is input to the amplifier 526. The amplifier 526 amplifies the output signal to a level appropriate for inputting the output signal to the downstream AD converter 528.

The amplified output signal is input to the direct-current conversion unit 527, which converts the alternate current output signal to a direct current signal. Thereafter, the output signal is input to the AD converter 528, which converts the analog output signal to a digital signal.

The output signal converted to a digital format is input to the CPU 529. At the same time, the output signal acquired when the capsule medical device 10 is not disposed is input from the memory 531 connected to the CPU 529 to the CPU 529.

The CPU 529 computes a difference between the two input output signals to obtain an output signal related to the induction magnetic field. Subsequently, the CPU 529 performs computation for determining the position of the internal coil 10a, that is, the position of the capsule medical device 10 on the basis of the obtained output signal related to the induction magnetic field. Any known computation method can be applied to the computation for determining the position of the capsule medical device 10.

The operation for guiding the capsule medical device is described next.

Information about the desired movement of the capsule medical device 10 is input to the input unit 517 in order to remotely control the capsule medical device 10. The input unit 517 outputs a signal to the guiding control unit 516 on the basis of the input information. The guiding control unit 516 generates a control signal for producing a magnetic field on the basis of the input signal so as to physically move the capsule medical device 10. Thereafter, the guiding control unit 516 outputs the control signal to the signal generators 513D, 514D, and 515D.

The signal generators 513D, 514D, and 515D generate signals to be output to the guiding magnetic field generating coil driving units 513C, 514C, and 515C on the basis of the input control signal. The guiding magnetic field generating coil driving units 513C, 514C, and 515C current-amplify the input signals and apply the electrical currents to the guiding magnetic field generating coils 513A and 513B, the guiding magnetic field generating coils 514A and 514B, and the guiding magnetic field generating coils 515A and 515B.

As noted above, by applying the electrical currents to the guiding magnetic field generating coils 513A and 513B, the guiding magnetic field generating coils 514A and 514B, and the guiding magnetic field generating coils 515A and 515B, the guiding magnetic fields can be generated in the vicinity of the capsule medical device 10. These generated magnetic fields can move a magnet in the capsule medical device 10. By moving the magnet, the capsule medical device 10 can be moved.

The operation performed when the mutual induction magnetic fields are generated by the guiding magnetic field generating coils 513A and 513B, the guiding magnetic field generating coils 514A and 514B, and the guiding magnetic field generating coils 515A and 515B is described next. This operation is the specific feature of the present invention.

The magnetic flux of the alternating magnetic field emanating from the position detecting magnetic field generating coil 11 passes through the guiding magnetic field generating coil 513A disposed in the vicinity of the position detecting magnetic field generating coil 11. At that time, since the magnetic flux passes through the guiding magnetic field generating coil 513A, a magnetic field in a direction that cancels out the change in the strength of the magnetic field, that is, an induced electromotive force that forms a reversed-phase magnetic field whose phase is opposite that of the alternating magnetic field is generated.

Since the guiding magnetic field generating coils 513A and 513B are driven by the different guiding magnetic field generating coil driving units 513C-1 and 513C-2, respectively, the induced electromotive force produced in the guiding magnetic field generating coil 513A causes an electrical current to flow in a closed circuit formed by the guiding magnetic field generating coil driving unit 513C-1 and the guiding magnetic field generating coil 513A. Therefore, a reversed-phase magnetic field whose phase is opposite that of the position detecting magnetic field is formed. In contrast, since that electrical current does not flow in the guiding magnetic field generating coil 513B, a reversed-phase magnetic field whose phase is opposite that of the position detecting magnetic field is not formed in the vicinity of the magnetic field sensor 12.

In such a configuration, the position detecting magnetic field generating coil 11 generates a position detecting magnetic field that induces an induced magnetic field in the internal coil 10a included in the capsule medical device 10. The induced magnetic field emanating from the internal coil 10a is detected by the magnetic field sensor 12 and is used for detecting the position or the attitude of the capsule medical device 10 including the internal coil 10a.

In addition, the guiding magnetic fields generated by a pair of the guiding magnetic field generating coils 513A and 513B, a pair of the guiding magnetic field generating coils 514A and 514B, and a pair of the guiding magnetic field generating coils 515A and 515B act on the magnet included in the capsule medical device 10 and control the position or the attitude of the capsule medical device 10. Here, since the center axis lines of the pair of guiding magnetic field generating coils 513A and 513B, the pair of guiding magnetic field generating coils 514A and 514B, and the pair of guiding magnetic field generating coils 515A and 515B are perpendicular to each other, the magnetic field lines of the guiding magnetic field can be three-dimensionally directed in any direction. Thus, the position or the attitude of the capsule medical device 10 including the magnet can be three-dimensionally controlled.

Furthermore, the two guiding magnetic field generating coils 513A and 513B are driven by the guiding magnetic field generating coil driving units 513C-1 and 513C-2, respectively. Accordingly, even under the condition in which the position detecting magnetic field induces a mutual induction magnetic field in the guiding magnetic field generating coil 513A, an electrical current generated by an electromotive force induced by the guiding magnetic field generating coil 513A does not flow in the guiding magnetic field generating coil 513B. Consequently, the guiding magnetic field generating coil 513B generates only a guiding magnetic field without generating the mutual induction magnetic field having a phase reversed to that of the position detecting magnetic field. As a result, a magnetic field that cancels out the position detecting magnetic field does not generated by the guiding magnetic field generating coil 513B, and therefore, formation of an area in which the strength of the position detecting magnetic field is substantially zero can be prevented.

The technical scope of the invention is not limited to any of the above-described embodiments. Many modifications are possible which remain within the concept, scope, and spirit of the invention.

For example, while the above-described embodiments have been described with reference to the configuration in which a magnetic field generating coil, a magnetic sensor, and a reversed-phase magnetic field generating coil are arranged substantially in a line, the present invention is not limited to such a configuration. For example, a plurality of magnetic field generating coils may be arranged in a plurality of lines. In addition, any number of the magnetic field generating coils may be arranged at any positions.

In addition, while the above-described embodiments have been described with reference to the capsule medical device that captures images in the body cavity of a subject as a medical device, the application is not limited to the capsule medical device serving as an endoscopic capsule. For example, the present invention is applicable to a variety of medical devices, such as a medical device that releases medicine in the body cavity of a subject, a medical device including a sensor that acquires data about the body cavity, a medical device disposed in the body cavity for a predetermined period of time, or a medical device having a wiring connected thereto in order to exchange information with an external apparatus.

What is claimed is:

1. A medical-device magnetic guiding and position detecting system comprising:
   a medical device capable of being disposed in the body of a subject, the medical device including at least one magnet and a circuit including an internal coil;
   a first magnetic field generating unit disposed outside a subject in order to generate a first magnetic field that acts on the internal coil;
   a magnetic field sensor for detecting an induction magnetic field induced in the internal coil due to the first magnetic field;
   a position detecting means for acquiring position information of the internal coil on the basis of the detected information from the magnetic field sensor;
   at least one pair of opposing coils for generating a second magnetic field that acts on the at least one magnet to guide the medical device; and
   a plurality of coil driving units for driving the opposing coils;
   wherein one opposing coil of the at least one pair of opposing coils is disposed opposite to an other opposing coil of the at least one pair of opposing coils with the medical device interposed therebetween,
   the first magnetic field generating unit is disposed on substantially the same plane as that on which the one opposing coil is disposed or in the vicinity of the other opposing coil,
   the magnetic field sensor is disposed on substantially the same plane as that on which the one opposing coil is disposed or in the vicinity of the other opposing coil, and
   the opposing coils forming each of the at least one pair are independently driven by the respective coil driving units for preventing the other opposing coil from generating a mutual induction magnetic field which has an opposite phase to the first magnetic field which is generated by having the magnetic field which is generated from the first magnetic field generating unit pass through the one opposing coil.

2. A medical-device magnetic guiding and position detecting system comprising:
   a medical device capable of being disposed in the body of a subject, the medical device including at least one magnet and a circuit including an internal coil;
   a first magnetic field generating unit disposed outside a subject in order to generate a first magnetic field that acts on the internal coil;
   a magnetic field sensor for detecting an induction magnetic field induced in the internal coil due to the first magnetic field;
   a position detecting means for acquiring position information of the internal coil on the basis of the detected information from the magnetic field sensor;
   at least one pair of opposing coils for generating a second magnetic field that acts on the at least one magnet to guide the medical device; and
   a switching unit electrically connected to the at least one pair of opposing coils;
   wherein one opposing coil of the at least one pair of opposing coils is disposed opposite to an other opposing of opposing coils with the medical device interposed therebetween,
   the first magnetic field generating unit is disposed on substantially the same plane as that on which the one opposing coil is disposed or in the vicinity of the opposing coil,
   the magnetic field sensor is disposed on substantially the same plane as that on which the one opposing coil is disposed or in the vicinity of the other opposing coil, and
   the switching unit is in a disconnecting mode only when the position detecting means detects the position of the internal coil.

3. A medical-device magnetic guiding and position detecting system comprising:
   a medical device capable of being disposed in the body of a subject, the medical device including at least one magnet and a circuit including an internal coil;
   a first magnetic field generating unit disposed outside a subject in order to generate a first magnetic field that acts on the internal coil;
   a magnetic field sensor for detecting an induction magnetic field induced in the internal coil due to the first magnetic field;
   position detecting means for acquiring position information of the internal coil on the basis of the detected information from the magnetic field sensor;
   at least one pair of opposing coils for generating a second magnetic field that acts on the at least one magnet to guide the medical device; and
   an element having two terminals and having an impedance lower than an impedance of one of the opposing coils forming each of the at least one pair at least at a frequency of the first magnetic field, the element having an impedance higher than an impedance of the other opposing coil at least at a frequency of the second magnetic field;
   wherein one opposing coil of the at least one pair of opposing coils is disposed opposite to an other opposing coil of the at least one pair of opposing coils with the medical device interposed therebetween, the first magnetic field generating unit is disposed on substantially the same plane as that on which the one opposing coil is disposed or in the vicinity of the other opposing coil, the magnetic field sensor is disposed on substantially the same plane as that on which the one opposing coil is disposed or in the vicinity of the other opposing coil, and the opposing coils forming each of the at least one pair form a series-connected circuit, and one terminal of the element is connected to a point between the opposing coils of each of the at least one pair, and the other terminal of the element is connected to ground.

4. The medical-device magnetic guiding and position detecting system according to claim 3, wherein the frequency of the first magnetic field is higher than the frequency of the second magnetic field.

5. The medical-device magnetic guiding and position detecting system according to claim 3, wherein the element is a series resonance circuit that produces resonance at a resonance frequency and the resonance frequency of the series resonance circuit is substantially the same as the frequency of the first magnetic field.

6. The medical-device magnetic guiding and position detecting system according to any one of claims 1, 2 and 3-5, wherein at least three pairs of opposing coils are disposed around an area where the at least one magnet is disposed, the first magnetic field generating unit includes a magnetic field generating coil disposed in the vicinity of one of the opposing coils forming at least one pair, the position detecting means includes a magnetic field sensor disposed in the vicinity of the other opposing coil forming the at least one pair, and the direction of a center axis of at least one pair among the at least three pairs of opposing coils crosses a plane formed by center axes of the other two pairs of opposing coils.

* * * * *